United States Patent
Phiel et al.

(10) Patent No.: US 7,378,111 B2
(45) Date of Patent: May 27, 2008

(54) REGULATION OF GSK-3α ACTIVITY FOR THE TREATMENT OR PREVENTION OF ALZHEIMER'S DISEASE

(75) Inventors: Christopher J. Phiel, Royersford, PA (US); Christina A. Wilson, Lansdowne, PA (US); Virginia M-Y. Lee, Philadelphia, PA (US); Peter S. Klein, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 356 days.

(21) Appl. No.: 10/368,769

(22) Filed: Feb. 19, 2003

(65) Prior Publication Data

US 2004/0110837 A1 Jun. 10, 2004

Related U.S. Application Data

(60) Provisional application No. 60/359,290, filed on Feb. 20, 2002.

(51) Int. Cl.
*A61K 33/14* (2006.01)
*A61K 33/00* (2006.01)
*A61P 25/28* (2006.01)

(52) U.S. Cl. .................. 424/677; 424/722; 514/879

(58) Field of Classification Search ................ 424/677, 424/722; 514/879
See application file for complete search history.

(56) References Cited

U.S. PATENT DOCUMENTS

| | | | |
|---|---|---|---|
| 4,160,152 A | 7/1979 | Wightman et al. | |
| 4,256,108 A | 3/1981 | Theeuwes | |
| 4,265,874 A | 5/1981 | Bonsen et al. | |
| 4,556,068 A | 12/1985 | Vartsky et al. | |
| 4,777,049 A | 10/1988 | Magruder et al. | |
| 4,810,497 A * | 3/1989 | Horrobin | 424/677 |
| 5,252,333 A | 10/1993 | Horrobin | |
| 6,057,117 A | 5/2000 | Harrison et al. | |
| 6,160,018 A | 12/2000 | Wechter et al. | |
| 6,335,034 B1 | 1/2002 | Drizen et al. | |
| 6,375,990 B1 | 4/2002 | Nemeroff et al. | |
| 6,441,053 B1 | 8/2002 | Klein et al. | |
| 6,517,859 B1 | 2/2003 | Tice et al. | |
| 2001/0052137 A1 | 12/2001 | Klein | |

OTHER PUBLICATIONS

Kalback, W. et al., "APP transgenic mice Tg2576 accumulateAβ peptides that are distinct from the chemically modified and insoluble peptides deposited in Alzheimer's Disease senile plaques," Biochemistry, vol. 41, pp. 922-928 (2002).*
Alvarez, G., et al., "Regulation of tau phosphorylation and protection against beta-amyloid-induced neurodegeneration by lithium. Possible implications for Alzheimer's disease," Bipolar Disord. 4:153-165 (2002).
Bunny, et al., In: *Psychopharmacology: The Third Generation of Progress* (Hy, ed.) New York, Raven Press 553-565, date unavailable.
Cook, D.G. et al., "Alzheimer's A beta(1-42) is generated in the endoplasmic reticulum/ intermediate compartment of NT2N cells," *Nat. Med.* 3:1021-1023 (1997).
De Strooper, B. et al., "A presenilin-1-dependent gamma-secretase-like protease mediates release of Notch intracellular domain," *Nature* 398:518-522 (1999).
De Strooper, B. et al., "Deficiency of presenilin-1 inhibits the normal cleavage of amyloid precursor protein," *Nature* 391:387-390 (1998).
Edbauer, D., et al., "Presenilin and nicastrin regulate each other and determine amyloid beta-peptide production via complex formation," *Proc. Nat'l. Acad. Sci. USA* 99:8666-8671 (2002).
Embi, et al., "Glycogen Synthase Kinase-3 from Rabbit Skeletal Muscle," *Eur. J. Biochem.* 107:519-527 (1980).
Elbashir, S.M. et al., "Duplexes of 21-nucleotide RNAs mediate RNA interference in cultured mammalian cells," *Nature* 411:494-498 (2001).
Esler, W.P., et al., "Activity-dependent isolation of the presenilin-gamma-secretase complex reveals nicastrin and a gamma secretase substrate," *Proc. Nat'l. Acad. Sci. U S A* 99:2720-2725 (2002).
Fagatto, et al., "Binding to Cadherins Antagonizes the Signaling Activity of B-Catenin during Axis Formation in *Xenopus*," J. Cell Biol. 132:1105-1114 (1996).
Forman, M.S., et al., "Differential effects of the Swedish mutant amyloid precursor protein on beta-amyloid accumulation and secretion in neurons and nonneuronal cells," *J. Biol. Chem.* 272:32247-32253 (1997).
Francis, R., et al., "aph-1 and pen-2 are required for Notch pathway signaling,gamma-secretase cleavage of beta APP, and presenilin protein accumulation," *Dev. Cell* 3:85-97 (2002).
Genaro, Remington's Pharmaceutical Sciences, Mack Publishing Co., Easton, PA (1985).
Goodwin, et al., In: *Manic-Depressive Illness*, New York Oxford University Press, date unavailable.
*Handbook of Dementing Illnesses* (John Morris Ed.) Marcel Dekker p. 591 (1994).

(Continued)

*Primary Examiner*—John Pak
(74) *Attorney, Agent, or Firm*—Evelyn H. McConathy; Montgomery, McCracken, Walker & Rhoads, LLP

(57) ABSTRACT

Provided is a novel use of therapeutic concentrations of an inhibitor of glycogen synthase kinase-3 (GSK-3), including lithium or any other GSK-3 inhibitor, to block, reduce or inhibit processing of amyloid precursor proteins to beta-amyloid (Aβ) peptides, which are now believed to be the principal cause of Alzheimer's disease, thereby providing methods useful for the prevention, inhibition or reversal of the disease. Also provided are methods of using agents that specifically target the α isoform of GSK-3, which is responsible for APP processing, making such selective GSK-3α-specific inhibitors especially useful in the treatment, prevention, and possible reversal of Alzheimer's disease. Further provided are kits and screening methods associated with the present methods.

7 Claims, 7 Drawing Sheets

OTHER PUBLICATIONS

Hardy, et al., "Evaluation of an enteric-coated delayed-release 5-aminosalicylic acid tablet in patients with inflammatory bowel disease," *Aliment. Pharmacol. Therap.* 1:273-280 (1987).

Harlow and Lane (eds.) In: *Antibodies: A Laboratory Manual*, Cold Spring Harbor Laboratory Press, NY (1998).

Harwood, et al., "Glycogen Synthase Kinase 3 Regulates Cell Fate in Dictyostelium," *Cell* 80:139-148 (1995).

Hemmings, et al., "Purification of Glycogen Synthase Kinase 3 from Rabbit Skeletal Muscle," *Eur. J. Biochem.* 119:445-451 (1982).

Hedgepeth, C. M., et al., "Activation of the Wnt Signaling Pathway: A Molecular Mechanism for Lithium Action," *Devl. Biol.* 185:82-91 (1997).

Hoeflich, K.P. et al., "Requirement for glycogen synthase kinase-3beta in cell survival and NF-kappa B activation," *Nature* 406:86-90 (2000).

Hunter, T., et al., "The Protein Kinases of Budding Yeast: Six Score and More," *TIBS* 22:18-22 (1997).

Iwatsubo, T. et al., "Visualization of A beta 42(43) and A beta 40 in senile plaques with end-specific A beta monoclonals:evidence that an initially deposited species is A beta 42(43)," *Neuron* 13:45-53 (1994).

Jope, et al., "Commentary: Lithium and Brain Signal Transduction Systems," *Biochem. Pharmacol.* 47:429-441 (1994).

Kang, D.E., et al., "Presenilin couples the paired phosphorylation of beta-catenin independent of axin:implications for beta-catenin activation in tumorigenesis," *Cell* 110:751-762 (2002).

Kang, D.E. et al., "Presenilin 1 facilitates the constitutive turnover of beta-catenin:differential activity of Alzheimer's disease-linked PS1 mutants in the beta-catenin-signaling pathway," *J. Neurosci.* 19:4229-4237 (1999).

Kirschenbaum, F., et al., "Substitution of a glycogen synthase kinase-3beta phosphorylation site in presenilin 1 separates presenilin function from beta-catenin signaling," *J. Biol. Chem.* 276:7366-7375 (2001).

Klein, P. S., et al., "A Molecular Mechanism for the Effect of Lithium on Development," *Proc. Natl. Acad. Sci. USA* 93:8455-8459 (1996).

Korinek, et al., "Constitutive transcriptional activation by a β-Catenin-Tcf complex in APC-/- colon carcinoma," *Science* 275:1784-1787 (1997).

Leclerc, S. et al., "Indirubins inhibit glycogen synthase kinase-3 beta and CDK5/p25, two protein kinases involved in abnormal tau phosphorylation in Alzheimer's disease. A property common to most cyclin-dependent kinase inhibitors?" *J. Biol. Chem.* 276:251-260 (2001).

Lee, et al., "Secretion and Intracellular Generation of Truncated AB in B-Site Amyloid-B Precursor Protein-Cleaving Enzyme Expressing Human Neurons," *J. Biological Chem.*, 278(7)4458-4466 (2003).

Leost, M. et al., "Paullones are potent inhibitors of glycogen synthase kinase-3 beta and cyclin-dependent kinase 5/p25," *Eur. J. Biochem.* 267:5983-5994 (2000).

Miller, et al., "Signal Transduction through B-catenin and Specification of Cell Fate During Embryogenesis," *Genes & Dev.* 10:2527-2539 (1996).

Phiel, C.J., et al., "Molecular Targets of Lithium Action," *Annu. Rev. Pharmacol. Toxicol.* 41:789-813 (2001).

Physicians Desk Reference 2352, 2658 (1997).

Pleasure, S.J., et al., "Pure, postmitotic, polarized human neurons derived from NTera 2 cells provide a system for expressing exogenous proteins in terminally differentiated neurons," *J. Neurosic.* 12:1802-1815 (1992).

Plyte, et al., "Glycogen Synthase Kinase-3: Functions in Oncogenesis and Development," *Biochem. Biophys. Act.* 1114:147-162 (1992).

Price, et al., "Drug Therapy: Lithium In the Treatment of Mood Disorders," *New Engl. J. Med.* 331:591-598 (1994).

Ramakrishna, et al., "Effect of Insulin on ATP-Citrate Lyase Phosphorylation: Regulation of Peptide A and Peptide B Phosphorylations," *Biochem.* 28:856-860 (1989).

Ramakrishna, et al., "Cyclic Nucleotide-independent Protein Kinas from Rate Liver," *J. Biol. Chem.* 260:12280-12286 (1985).

Risby, et al., "The Mechanisms of Action of Lithium," *Arch. Gen. Psychiatry* 48:513-524 (1991).

Sahasrabudhe, et al., "Release of Amino-terminally Fragments from Amyloid Precursor Protein Reporter and Mutated Derivatives in Cultured Cells," *J. Biol Cell* 267:25602-25608 (1992).

Schroeter, E.H., et al., "Notch-1 signalling requires ligand-induced proteolytic release of intracellular domain," *Nature* 393:382-386 (1998).

Selkoe, D.J., "Presenilin, Notch, and the genesis and treatment of Alzheimer's disease," *Proc. Nat'l. Acad. Sci. USA* 98:11039-11041 (2001).

Siman, R., et al., "Presenilin-1 P264L knock-in mutation: Differential effects on A beta production, amyloid deposition,and neuronal vulnerability," *J. Neurosci.* 20:8717-8726 (2000).

Soriano, S., et al., "Presenilin 1 negatively regulates beta-catenin/T cell factor/lymphoid enhancer factor-1 signaling independently of beta-amyloid precursor protein and notch processing," *J. Cell Biol.* 152:785-794 (2001).

Stambolic, et al., "Lithium Inhibits Glycogen Synthase Kinase-3 Activity and Mimics Wingless Signalling in Intact Cells," *Current Biology* 6(12):1664-1668 (1996).

Sun, et al., Glycogen Synthase Kinase-3B Is Complexed with Tau Protein in Brain Microtubules, *J. Biol Chem.* 277(14): 11933-11940 (2002).

Sun, X., Sato, S., Murayama, O., Murayama, M., Park, J.-M., Yamaguchi, H., Takashima, A., "Lithium inhibits amyloid secretion in COS7 cells transfected with amyloid precursor protein C100," *Neurosci. Lett.* 321:61-64 (2002).

Suzuki, N. et al., "An increased percentage of long amyloid beta protein secreted by familial amyloid beta protein precursor (beta APP717) mutants," *Science* 264:1336-1340 (1994).

Takashima, A. et al., "Presenilin 1 associates with glycogen synthase kinase-3 beta and its substrate tau," *Proc. Nat'l. Acad. Sci. USA* 95:9637-9641 (1998).

Turner, R.S., et al., "Amyloids beta40 and beta42 are generated intracellularly in cultured human neurons and their secretion increases with maturation," *J. Biol. Chem.* 271:8966-8970 (1996).

Vandenheede, et al., "ATP. Mg-dependent Protein Phosphatase from Rabbit Skeletal Muscle," *J. Biol. Chem.* 255:11768-11774 (1980).

Vassar, R. et al., "Beta-secretase cleavage of Alzheimer's amyloid precursorprotein by the transmembrane aspartic protease BACE," *Science* 286:735-741 (1999).

Weggen, S. et al., "A subset of NSAIDs lower amyloidogenic A beta42 independently of cyclooxygenase activity," *Nature* 414:212-216 (2001).

Wilson, C.A., et al., "Presenilins are not required for A beta42 production in the early secretory pathway," *Nat. Neurosci.* 5:849-855 (2002).

Wolfe, M.S. et al., "Two transmembrane aspartates in presenilin-1 required for presenilin endoproteolysis and gamma-secretase activity," *Nature* 398:513-517 (1999).

Wolfe, M.S. et al., "A substrate-based difluoro ketone selectively inhibits Alzheimer's gamma-secretase activity," *J. Med. Chem.* 41:6-9 (1998).

Wood, et al., "A review of the biochemical and neuropharmacological actions of lithium," *Psychol. Med.* 17:570-600 (1987).

Yu, G. et al., "Nicastrin modulates presenilin-mediated notch/glp-1 signal transduction and beta APP processing," *Nature* 407:48-54 (2000).

Zhang, Z. et al., "Destabilization of beta-catenin by mutations in presenilin-1 potentiates neuronal apoptosis," *Nature* 395:698-702 (1998).

* cited by examiner

SEQUENCE LISTING

```
<160> NUMBER OF SEQ ID NOS: 6

<210> SEQ ID NO 1
<211> LENGTH: 19
<212> TYPE: RNA
<213> ORGANISM: Artificial
<220> FEATURE:
<223> OTHER INFORMATION: Synthetic formulation

<400> SEQUENCE: 1
cuuacgcuga guacuucga                                           19

<210> SEQ ID NO 2
<211> LENGTH: 19
<212> TYPE: RNA
<213> ORGANISM: Artificial
<220> FEATURE:
<223> OTHER INFORMATION: Synthetic formulation

<400> SEQUENCE: 2
ucgaaguacu cagcguaag                                           19

<210> SEQ ID NO 3
<211> LENGTH: 19
<212> TYPE: RNA
<213> ORGANISM: Artificial
<220> FEATURE:
<223> OTHER INFORMATION: Synthetic formulation

<400> SEQUENCE: 3
aucuuuggag ccacugauu                                           19

<210> SEQ ID NO 4
<211> LENGTH: 19
<212> TYPE: RNA
<213> ORGANISM: Artificial
<220> FEATURE:
<223> OTHER INFORMATION: Synthetic formulation

<400> SEQUENCE: 4
```

-continued

```
aaucaguggc uccaaagau                                            19

<210> SEQ ID NO 5
<211> LENGTH: 19
<212> TYPE: RNA
<213> ORGANISM: Artificial
<220> FEATURE:
<223> OTHER INFORMATION: Synthetic formulation

<400> SEQUENCE: 5
uucuacucca guggugaga                                            19

<210> SEQ ID NO 6
<211> LENGTH: 19
<212> TYPE: RNA
<213> ORGANISM: Artificial
<220> FEATURE:
<223> OTHER INFORMATION: Synthetic formulation

<400> SEQUENCE: 6
ucucaccacu ggaguagaa                                            19
```

REGULATION OF GSK-3α ACTIVITY FOR THE TREATMENT OR PREVENTION OF ALZHEIMER'S DISEASE

REFERENCE TO RELATED APPLICATION

This application claims priority to U.S. Provisional Application No. 60/359,290, filed Feb. 20, 2002, the content of which is herein incorporated by reference.

GOVERNMENT INTEREST

This invention was supported in part by Grant Nos. AGI 1542 and RO1MH58324 from the National Institutes of Health. Accordingly, the Government may have certain rights in this invention.

FIELD OF THE INVENTION

The present invention relates to compositions and methods useful in the treatment and prevention of Alzheimer's disease, specifically relating to inhibiting the activity of glycogen synthase kinase-3 and/or glycogen synthase kinase-3α.

BACKGROUND OF THE INVENTION

Alzheimer's Disease (AD) is a degenerative brain disorder associated with extensive loss of specific neuronal cellular subpopulations, and characterized clinically by progressive loss of memory, cognition, reasoning, judgment and emotional stability that gradually leads to profound mental deterioration and ultimately death. The disease currently affects as many as four million individuals in the United States alone. To date, the disease has proven to be incurable, and presently causes up to 100,000 deaths annually.

The brains of individuals with AD exhibit neuronal degeneration and characteristic lesions variously referred to as amyloidogenic plaques, vascular amyloid angiopathy, and neurofibrillary tangles. It is presently believed that progressive cerebral deposition of particular amyloidogenic proteins, beta-amyloid proteins, play a seminal role in the pathogenesis of AD and can precede cognitive symptoms and onset of dementia by years or possibly even decades.

Alzheimer's disease is associated with aberrant processing of the amyloid precursor protein (APP), leading to increased production and aggregation of amyloid-β (Aβ) peptides. Amyloid plaques are composed primarily of 40 and 42 amino acid peptides (Aβ$_{40}$ and Aβ$_{42}$, respectively) (Selkoe, *Proc. Nat'l. Acad. Sci. USA* 98:11039-11041 (2001)) derived from APP by sequential proteolysis catalyzed by the aspartyl protease, BACE (Vassar et al., *Science* 286:735-741 (1999)), followed by presenilin-dependent γ-secretase cleavage (De Strooper et al., *Nature* 391:387-390 (1998)). Aβ$_{42}$ is less soluble than Aβ$_{40}$ and is the predominant Aβ species in amyloid plaques (Iwatsubo et al., *Neuron* 13:45-53 (1994)).

Presenilins 1 and 2 (PS1 and PS2) are integral membrane proteins proposed to have inherent γ-secretase activity (Wolfe et al., *Nature* 398:513-517 (1999)) and interact in a functional complex with nicastrin (Esler et al., *Proc. Nat'l. Acad. Sci. USA* 99:2720-2725 (2002); Edbauer et al., *Proc. Nat'l. Acad. Sci. USA* 99:8666-8671 (2002)), aph-1, and pen-2 (Francis et al., *Dev. Cell* 3:85-97 (2002)). Presenilins also interact with a number of other proteins, including α-catenin and β-catenin (Soriano et al., *J. Cell Biol.* 152: 785-794 (2001); Yu et al., *Nature* 407:48-54 (2000)). Presenilin 1, which is required for γ-secretase mediated processing of APP (De Strooper et al., 1998), interacts with glycogen synthase kinase-3 (GSK-3)(Takashima et al., *Proc. Nat'l. Acad. Sci. USA* 95:9637-9641 (1998); Kang et al., *J. Neurosci.* 19:4229-4237 (1999); Kang et al., *Cell* 110:751-762 (2002)), although a functional role for this proteins in γ-secretase function has not been previously established.

Glycogen synthase kinase-3 (GSK-3) is a serine/threonine protein kinase having a monomeric structure and a size of approximately 47 kilodaltons. It is one of several protein kinases which phosphorylate glycogen synthase (Embi et al., *Eur. J. Biochem.* 107:519-527 (1980); Hemmings et al., *Eur. J. Biochem.* 119:443-451 (1982)). GSK-3 is also referred to in the literature as factor A ($F_A$) in the context of its ability to regulate $F_C$, a protein phosphatase (Vandenheede et al., *J. Biol. Chem.* 255:11768-11774 (1980)). Other names for GSK-3 and homologs thereof include: zeste-white3/shaggy (zw3/sgg; the *Drosophila melanogaster* homolog), ATP-citrate lyase kinase (ACLK or MFPK; Ramakrishna et al., *Biochem.* 28:856-860 (1989); Ramakrishna et al., *J. Biol. Chem.* 260:12280-12286 (1985), GSKA (the Dictyostelum homolog; Harwood et al., *Cell* 80:139-48 (1995), and MDSI, MCK1, and others (yeast homologs; Hunter et al., *TIBS* 22:18-22 (1997)), tau protein kinase (mammalian) and GSKA (Dictyostelium).

The gene encoding GSK-3 is highly conserved across diverse phyla. In vertebrates, GSK-3 exists in two isoforms, designated GSK-3α (51 kDa) and GSK-3β (47 kDa). These two isoforms are the products of distinct genes. The amino acid identity among vertebrate homologs of GSK-3 is in excess of 98% within the catalytic domain (Plyte et al., *Biochim. Biophys. Acta* 1114:147-162 (1992)), although GSK-3α is known to be slightly larger than GSK-3β.

Sun et al., *J. Biol. Chem.* 277(14):11933-11940 (April 2002) have reported that in brain extracts and in MAP fractions, the amounts of GSK-3α and GSK-3β are almost equal, but that there are profound differences between the amounts of each kinase complexed with tau, further distinguishing the functions of the two. The authors determined that 6-fold more tau is complexed with GSK-3β than with GSK-3α in the brain, and that GSK-3β is bound to tau within an approximately 400-kDa micro-tubule-associated complex. Thus, GSK-3β associates with the microtubules via tau.

GSK-3 phosphorylates numerous proteins in vitro, including beta-catenin, glycogen synthase, phosphatase inhibitor I-2, the type-II subunit of cAMP-dependent protein kinase, the G-subunit of phosphatase-1, ATP-citrate lyase, acetyl coenzyme A carboxylase, myelin basic protein, a microtubule-associated protein, a neurofilament protein, an N-CAM cell adhesion molecule, nerve growth factor receptor, c-Jun transcription factor, JunD transcription factor, c-Myb transcription factor, c-Myc transcription factor, L-myc transcription factor, adenomatous polyposis coli tumor suppressor protein, and tau protein (Plyte et al., 1992; Korinek et al., *Science* 275:1784-1787 (1997); Miller et al., *Genes & Dev.* 10:2527-2539 (1996)). The phosphorylation site recognized by GSK-3 has been determined in several of these proteins (Plyte et al., 1992). The diversity of these proteins suggests a wide role for GSK-3 in the control of cellular metabolism, regulation, growth, and development. GSK-3 tends to phosphorylate serine and threonine residues in a proline-rich environment, but does not display the absolute dependence upon these amino acids which is displayed by protein kinases which are members of the mitogen-activated protein (MAP) kinase or cdc2 families of kinases.

U.S. Pat. No. 6,441,053 (Klein et al.) teaches a method of identifying inhibitors of GSK-3 and for treating a GSK-3-related disorders—other than Alzheimer's disease in an animal. The method comprises providing a mixture comprising GSK-3, a phosphate source, and a GSK-3 substrate, incubating the mixture in the presence or absence of a test compound, and assessing the activity of GSK-3 in the mixture. A reduction of GSK-3 activity following incubation of the mixture in the presence of the test compound is an indication that the test compound is an inhibitor of GSK-3. In the '053 patent, however, the GSK-3 inhibitor is expressly not lithium.

U.S. Pat. No. 6,057,117 (Harrison et al.) teaches a pharmaceutical composition comprising a selective GSK-3 inhibitor identified by: (a) contacting a first radiolabeled peptide substrate comprising an isolated nucleotide sequence, in which the N-terminal serine is the target of phosphorylation by GSK-3 and the C-terminal serine is prephosphorylated, coupled to an anchor ligand with GSK-3 in the presence of radiolabeled phosphate-$\gamma$ATP, a substrate anchor, and a candidate inhibitor, then (b) contacting a second radiolabeled peptide substrate coupled to an anchor ligand with GSK-3 in the presence of radiolabeled phosphate-$\gamma$ATP, and a substrate anchor, and (c) identifying an inhibitor of GSK-3 kinase activity by a reduction of radiolabel incorporation in step (a) compared to step (b). The identified composition is also used to treat a subject having a condition mediated by GSK-3 activity or susceptible to such a condition. In an alternative embodiment of the '117 patent a second therapeutic compound may be added, wherein the compound may be lithium. However, no lithium therapy is suggested with regard to blocking or inhibiting the activity of the GSK-3$\alpha$ isoform. See also Stambolic et al., Current Biology 6(12): 1664-1668 (1996).

The activity of both GSK-3$\alpha$ and -3$\beta$ has been reported to be inhibited by lithium (e.g., Klein et al., Proc. Natl. Acad. Sci. USA 93:8455-8459 (1996); Hedgepeth et al., Dev. Biol. 185:82-91(1997); Phiel et al., Annu. Rev. Pharmacol. Toxicol. 41:789-813 (2001); U.S. Publ. Patent Appl. 20010052137 (Klein et al.)), yet specific inhibitors of the activity of the GSK-3$\alpha$ isoform alone (without affecting GSK-3$\beta$) remain unknown. Inhibition of GSK-3$\beta$ is a physiological mechanism by which lithium exerts its therapeutic effects in animals (e.g., humans) afflicted with a variety of disorders. For example, lithium is an effective drug for treatment of bipolar (manic-depressive) disorder (Price et al., New Eng. J. Med. 331:591-598 (1994); Goodwin et al., (1990) In: Manic-Depressive Illness, New York: Oxford University Press), and can be used to treat profound depression in some cases, although it is not known whether lithium works through GSK-3 in the treatment of bipolar disorder. Despite the remarkable efficacy of lithium observed during decades of its use, the molecular mechanism(s) underlying its therapeutic actions have not been fully elucidated (Bunney et al., (1987) In: Psychopharmacology: The Third Generation of Progress, (Hy, ed.) New York, Raven Press, 553-565; Jope et al., Biochem. Pharmacol. 47:429-441 (1994); Risby et al., Arch. Gen. Psychiatry 48:513-524 (1991); Wood et al., Psychol. Med. 17:570-600 (1987)).

Lithium is a fixed monovalent cation and the lightest of the alkali metals (group 1a of the Periodic Table of the elements). $Li^+$ has the highest energy of hydration of the alkali metals and, as such, can substitute for $Na^+$ (and to a lesser extent $K^+$) for ion transport by biological systems. Lithium is both electroactive and hydrophilic, and trace amounts of $Li^+$ are found in human tissues; typical human blood plasma concentrations of $Li^+$ are about 17 µg/L.

Unlike other psychotropic drugs, $Li^+$ has no discernible psychotropic effects in normal man, although the therapeutic efficacy of lithium in the treatment of acute mania and the prophylactic management of bipolar (manic/depressive) disorder has been consistently demonstrated. The oral and parenteral administration of lithium salts, such as lithium carbonate and lithium citrate, has also found widespread use in the current treatment of, for example, alcoholism, aggression, schizophrenia, unipolar depression, skin disorders, immunological disorders, asthma, multiple sclerosis, rheumatoid arthritis, Crohn's disease, ulcerative colitis, and irritable bowel syndrome, as well as for use in many other diseases and conditions.

Unfortunately, no drug treatments for Alzheimer's disease have, to date, proven to be very satisfactory, and demonstrating the effectiveness of such drugs in the treatment of dementias can be quite difficult, see, e.g., Handbook of Dementing Illnesses, (John Morris, Ed.), Marcel Dekker 1994, p. 591. Part of this difficulty arises from the fact that it can often be difficult to clearly diagnose the type of dementia with which the patient is afflicted. Thus, there exists a pressing need to identify compositions that have a blocking or inhibiting effect in humans on the control of GSK-3$\alpha$ specifically required for APP processing to (A$\beta$) peptides, and/or to reduce formation of both amyloid plaques and neurofibrillary tangles, recognized as two pathological hallmarks of Alzheimer's disease. By finding a GSK-3$\alpha$-specific inhibitor, preferably that does not also affect GSK-3$\beta$, it will be possible to treat Alzheimer's disease in a patient without inhibiting GSK-3$\beta$, which serves many critical functions in cells.

SUMMARY OF THE INVENTION

The present invention provides a novel approach using therapeutic concentrations of an inhibitor of GSK-3 specifically to reduce processing of amyloid precursor proteins to beta-amyloid (A$\beta$) peptides, and thus to prevent, inhibit or reverse Alzheimer's disease. In one aspect of the invention, lithium treatment is shown to inhibit production of (A$\beta$) peptides in cultured cells, and in whole animals carrying familial Alzheimer's disease mutations. Moreover, this effect of lithium is mediated through the inhibition of GSK-3$\alpha$.

GSK-3 has previously been shown to phosphorylate tau protein, a component of paired helical filaments once thought to be a cause of Alzheimer's disease, and therefore GSK-3 inhibitors were proposed as potential therapy for Alzheimer's disease. However, no one has previously reported or suggested that GSK-3 inhibitors, such as lithium or any other GSK-3 inhibitor, act to block or inhibit the production of A$\beta$ peptides, which are now believed to be the principal cause of Alzheimer's.

Therapeutic concentrations of lithium block or inhibit production of A$\beta_{40}$ and A$\beta_{42}$ peptides by interfering with $\gamma$-secretase cleavage of APP, but they do not inhibit Notch processing. Notch is a distinct signaling molecule that is likely required for multiple functions. The fact that APP processing is blocked without affecting Notch processing means that one need not worry about potential side effects arising from inhibition of Notch processing. Importantly, the lithium compositions block accumulation of A$\beta$ peptides in the brains of mice that otherwise overproduce A$\beta$ peptides. Thus, in accordance with one aspect of the invention there are provided GSK-3 inhibitor compositions, e.g., a pharmaceutically acceptable lithium salt and a physiologically acceptable carrier, at therapeutically effective concentrations that are sufficient to inhibit, block, or even reverse, Aβ peptide accumulation.

A second important aspect of this invention was the discovery that the α isoform of GSK-3 (GSK-3α) is specifically responsible for APP processing. Therefore, agents that specifically target GSK-3α will be especially useful in the treatment, prevention, and possible reversal of Alzheimer's disease. Further provided are methods for treating a condition mediated by GSK-3α activity by administering a selective inhibitor of GSK-3α, which is preferably a therapeutically effective amount of a composition that specifically inhibits GSK-3α, but not GSK-3β or other lithium sensitive enzymes, or a pharmaceutically acceptable salt thereof, and a physiologically acceptable carrier.

Also included in the invention are methods of treating a GSK-3α-related disorder in an animal, comprising administering to the animal (or to the brain, brains cells or brain tissue of an animal) a GSK-3α inhibitor suspended in a pharmaceutically acceptable carrier. Preferably, the animal is a mammal, and more preferably, the mammal is a human. The GSK-3α related disorder, which is treated according to the methods of the invention, is preferably Alzheimer's disease. Nevertheless, selective inhibition of GSK-3α may be useful to treat or inhibit other disorders mediated by GSK-3α activity. Thus, the invention provides methods for treating a biological condition mediated by GSK-3α activity by administering an effective amount of a pharmaceutical composition comprising a selective GSK-3α inhibitor to a subject having a condition mediated by GSK-3α activity or susceptible to such a condition, e.g., Alzheimer's disease, wherein the production of Aβ peptides is blocked or inhibited.

The invention also provides an in vitro method of identifying an inhibitor of GSK-3α kinase activity that will block or inhibit the production of Aβ peptides, without blocking or inhibiting GSK-3β, and includes a pharmaceutical composition comprising an inhibitor identified by this in vitro method.

One aspect of the present invention provides methods for the treatment of a subject having Alzheimer's disease, or the conditions related thereto, wherein the methods comprise administering to the subject (or to a subject's brain cells or brain tissue) an inhibitor of GSK-3 kinase activity, such as lithium, in an amount sufficient to block or inhibit the production of Aβ peptides. Moreover, methods using those agents that specifically target GSK-3α to disrupt the γ-secretase mediated processing of APP will be especially useful in the treatment, prevention and possible reversal of Alzheimer's disease.

In accordance with still another aspect of the present invention, there are further provided methods for stabilizing a subject susceptible to Alzheimer's disease or the formation of amyloid plaques and neurofibrillary tangles or accumulated Aβ peptides (particularly $A\beta_{40}$ and $A\beta_{42}$ peptides) in the brain, thereby also stopping or inhibiting the processing of APP in the brain, or in brain cells or tissue, wherein the methods comprise administering to the subject a stabilizing amount of inhibitor of GSK-3 kinase activity, such as lithium, sufficient to block or inhibit the production of Aβ peptides. Further provided are methods using those agents that specifically target GSK-3α to disrupt the γ-secretase mediated processing of APP to stabilize the subject susceptible to Alzheimer's disease.

In accordance with yet another aspect of the present invention, there are provided methods for preventing Alzheimer's disease in a susceptible subject or preventing the formation of amyloid plaques and neurofibrillary tangles or accumulated Aβ peptides (particularly $A\beta_{40}$ and $A\beta_{42}$ peptides) in the brain, by administering an inhibitor of GSK-3 kinase activity, such as lithium, sufficient to block or inhibit the production of Aβ peptides. Also provided are methods using those agents that specifically target GSK-3α to disrupt the γ-secretase mediated processing of APP to prevent Alzheimer's disease in a subject susceptible to the disease.

In a further aspect of the present invention, there are provided methods for reversing the recognized hallmark effects in a subject having Alzheimer's disease, by preventing or inhibiting the continued formation of amyloid plaques and neurofibrillary tangles or accumulated Aβ peptides (particularly $A\beta_{40}$ and $A\beta_{42}$ peptides) in the brain, by administering an inhibitor of GSK-3 kinase activity, such as lithium, sufficient to block or inhibit the production of Aβ peptides causing a reversal of the Alzheimer's disease state, and/or using those agents that specifically target GSK-3α to disrupt the γ-secretase mediated processing of APP to further reverse the Alzheimer's disease state in the subject.

All combinations, sources and amounts of the active ingredients discussed herein in conjunction with the compositions of the present invention are contemplated as being administered in accordance with the method taught herein. Preferably the foregoing methods further comprise monitoring such subject's Aβ peptide levels, particularly $A\beta_{40}$ and $A\beta_{42}$ peptides, or GSK-3α levels, or the production or processing of APP. Included are in vivo and in vitro methods.

Further provided is a method of inhibiting or reducing symptoms of Alzheimer's disease in a patient, comprising the steps of:

(i) administering to the Alzheimer's disease patient a therapeutically effective composition, comprising a pharmaceutically acceptable amount of a GSK-3 inhibitor or GSK-3α-specific inhibitor, wherein the GSK-3 inhibitor or GSK-3α-specific inhibitor comprises lithium or a salt thereof;

(ii) measuring the blocking, inhibiting or reducing production of Aβ amyloid peptides in the patient following the administering step (i); and (iii) determining that the administered inhibitor is sufficient to block, inhibit or reduce GSK-3 or GSK-3α activity in the patient, such that measured formation of Aβ amyloid peptides in the patient is reduced in the ranges of 30% to 60%.

Also provided is a method of inhibiting or reducing symptoms of Alzheimer's disease in a patient, comprising the steps of:

(i) administering to the Alzheimer's disease patient a therapeutically effective composition, comprising a pharmaceutically acceptable amount of a GSK-3 inhibitor or GSK-3α-specific inhibitor, wherein the GSK-3 inhibitor or GSK-3α-specific inhibitor comprises lithium or a salt thereof;

(ii) measuring the blocking, inhibiting or reducing production of $A\beta_{40}$ and $A\beta_{42}$ peptide levels in the patient following the administering step (i); and (iii) determining that the administered inhibitor is effective for inhibiting or reducing symptoms of Alzheimer's disease in the patient, such that measured $A\beta_{40}$ and $A\beta_{42}$ peptide levels are reduced in the range of 30% to 60%.

Also provided are kits for administering an inhibitor of GSK-3 kinase activity, such as lithium, in an amount sufficient to block, reduce or inhibit the production of Aβ peptides in a subject of Alzheimer's disease, or one that is susceptible thereto, and/or for administering those agents that specifically target GSK-3α to disrupt the γ-secretase mediated processing of APP in the brain, brain cells or brain tissue of a subject.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE FIGURES

The foregoing summary, as well as the following detailed description of the invention, will be better understood when read in conjunction with the appended figures.

FIG. 1a is a histogram depicting the effect of treating CHO-APP$_{695}$ cells with sodium chloride (NaCl) or lithium chloride (LiCl), then measuring Aβ levels by an Aβ sandwich ELISA. The histogram represents normalized levels (fm Aβ/intracellular full length APP) of $A\beta_{40}$ (light bars) and $A\beta_{42}$ (dark bars). Error bars represent standard deviation. FIG. 1b depicts a PhosphorImager visualization of an SDS-PAGE separation of $^{35}$S-methionine labeled, immunoprecipitated Aβ secreted from CHO-APP$_{695}$ cells in the presence of LiCl (lane 2) or DFK-167 (lane 3). FIG. 1c depicts a PhosphorImager visualization of SDS-PAGE separated, immunoprecipitated intracellular APP holoprotein and C-terminal fragments (C99, C89, and C83) from CHO-APP$_{695}$ cells after treatment with LiCl or DFK-167. FIG. 1d depicts a western blot as assessed by myc (9E10), showing expression of Notch constructs (each having a C-terminal myc tag) after CHO-APP$_{695}$ cells were transfected with ΔE-Notch and treated with either LiCl or DFK-167 for 24 hours. Notch intracellular domain (ICD) beginning at residue 1744 is a positive control for cleavage (lane 2). ΔE-Notch V1744K with a point mutation in the γ-secretase cleavage site of ΔE-Notch is a negative control for cleavage (lane 3).

FIG. 2a graphically shows the effect of treating CHO-APP$_{695}$ cells with kenpaullone (a GSK-3 inhibitor), or with roscovitine (a cdk inhibitor that does not inhibit GSK-3). Secreted Aβ levels ($A\beta_{40}$=light bars; $A\beta_{42}$=dark bars). FIG. 2b depicts a western blot showing that in CHO-APP$_{695}$ cells treated with either kenpaullone or lithium, GSK-3 was inhibited, causing an accumulation of β-catenin protein. Roscovitine was added as a control. Western blot for actin is shown as a loading control. Con=untreated cells; D=DMSO control; Ken=kenpaullone; Rosco=roscovitine. FIG. 2c graphically shows the effect of transfecting CHO-APP$_{695}$ cells with a β-catenin-responsive luciferase reporter construct, OT-Luc (light bars), or with a mutated luciferase reporter, OF-Luc (dark bars), followed by treatment with LiCl, kenpaullone, or roscovitine. FIG. 2d graphically shows effect of overexpression of β-catenin on Aβ production. CHO-APP$_{695}$ cells were transfected with either GFP (control) or β-catenin in pCS2. Secreted $A\beta_{40}$=light bars and $A\beta_{42}$=dark bars. Inset in FIG. 2d shows western blot of endogenous GFP and overexpressed (β-cat) β-catenin in duplicate lanes.

FIG. 3a depicts a western blot for GSK-3α and GSK-3β of lysates from CHO-APP$_{695}$ cells transfected with siRNAs. siRNA against pGL3-luciferase (Pp-Luc) is control transfection. GSK-3α siRNA selectively reduces GSK-3β protein (closed arrow) and GSK-3β directed siRNA selectively reduces GSK-3β (open arrow). FIG. 3b graphically shows Aβ levels ($A\beta_{40}$=light bars; $A\beta_{42}$=dark bars) secreted from siRNA transfected cells. Error bars represent standard deviation. Asterisks indicate a significant difference from control, as determined by one-way ANOVA (p<0.05).

FIG. 4a shows the effect of lithium treatment on embryonic mouse cortical neurons infected with a Semliki Forest Virus containing either wild-type APP (APP-WT) or APP with the pathogenic Swedish mutation (KM670/671NL). $A\beta_{40}$=light bars; and $A\beta_{42}$=dark bars. FIGS. 4b and 4c show cortical $A\beta_{40}$ and $A\beta_{42}$ accumulation in both RIPA-extracted (soluble) and formic acid (FA)-extracted (insoluble) fractions of cortical tissue from lithium-treated or NaCl-treated subject animals that were heterozygous for both the APP-Swedish transgene (Tg2576) and the PS1 P264L knock-in. Error bars represent SEM. Asterisks in panel b and c denote significant difference from NaCl treated animals when assessed by a one-way ANOVA with p<0.05.

DESCRIPTION OF PREFERRED EMBODIMENTS OF THE INVENTION

Figure 1A:
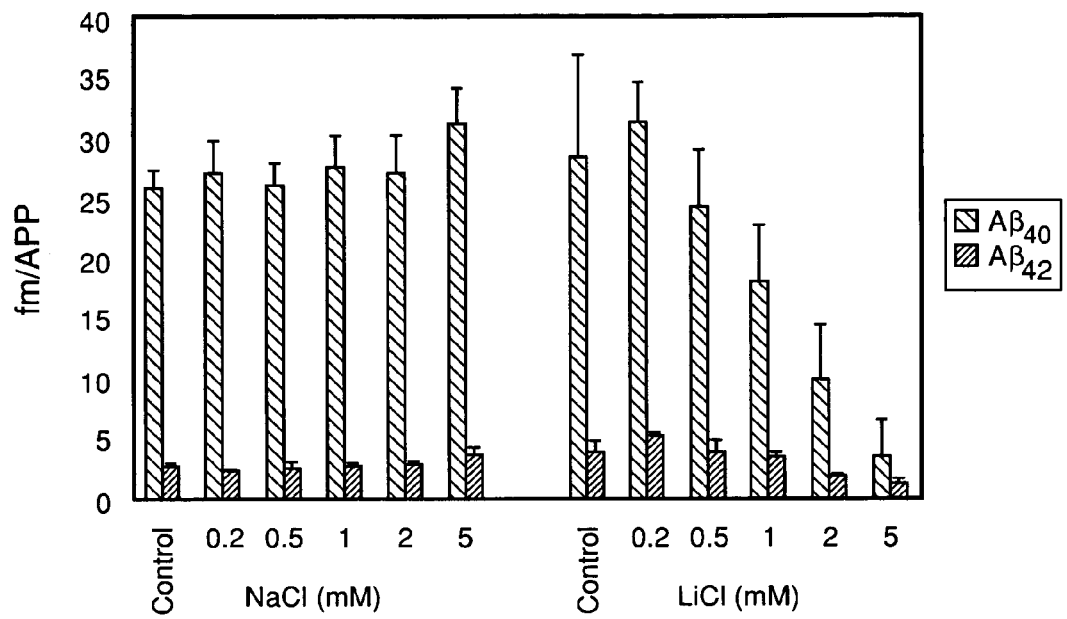
FIGS. 1a-1d show that lithium reduces secreted $A\beta_{40}$ and $A\beta_{42}$ levels in a dose-dependent manner and causes accumulation of APP C-terminal fragments.

The present invention provides a novel approach using an inhibitor of GSK-3 kinase activity, such as lithium, administered to a subject (or to the brain cells or brain tissues of a subject) sufficient to block or inhibit, or even reverse, the production of Aβ peptides in the brain, or brain cells or tissues, of the subject, thereby reducing the formation of both amyloid plaques and neurofibrillary tangles in the brains and brain tissue of Alzheimer's disease patients Thus, methods of the invention inhibit, prevent or reverse Alzheimer's disease in the subject as shown in the Examples that follow, wherein the production of (Aβ) peptides was inhibited in cultured cells by the administration of lithium, and in whole animals carrying familial Alzheimer's disease mutations. This effect of using GSK-3 inhibitors, such as lithium or any other GSK-3 inhibitor, to block, inhibit or reverse the production of Aβ peptides (now recognized as the principal cause of the Alzheimer's disease state), has never before been reported.

Moreover, this effect of lithium is mediated through the inhibition of GSK-3α.

Therapeutic concentrations of lithium block or inhibit production of $A\beta_{40}$ and $A\beta_{42}$ peptides by interfering with γ-secretase cleavage of APP, as shown in the Examples by the effect on CTF accumulation. Moreover, by using those agents that specifically target GSK-3α to disrupt the γ-secretase mediated processing of APP, the Alzheimer's disease state in the subject (or in the brain cells or tissue of the subject) is treated, prevented, or even in some cases, reversed. It further blocks or inhibits generation of Aβ peptides through inhibition of GSK-3α, or reduces those Aβ peptides that have already begun to form. In support of this conclusion: 1) lithium was shown to reduce Aβ production in cultured cells and in the brains of mice that overproduce Aβ peptides; 2) kenpaullone, an alternative GSK-3α inhibitor that acts through a distinct mechanism, also inhibits Aβ production; 3) RNAi mediated depletion of GSK-3α reduces Aβ production; and 4) moderate overexpression of GSK-3α increases Aβ production. Furthermore, when lithium is administered as a GSK-3α inhibitor, it inhibits APP processing at the γ-secretase step.

In contrast, in the examples that follow, it is shown that reduction of GSK-3β does not attenuate, and may enhance, Aβ production. These observations are surprising, as the sequences of GSK-3α and β are 97% identical within the kinase domains and appear to be redundant in the Wnt pathway, although not in the regulation of NF-KB (Hoeflich et al., *Nature* 406:86-90 (2000)). However, the amino-and carboxy-terminal sequences of GSK-3α and GSK-3β are quite dissimilar, and this divergence may account for functional differences in the regulation of APP processing, perhaps reflecting differences in protein-protein interactions.

A number of molecules have been identified recently that are required in addition to presenilin for γ-secretase activity, including nicastrin (Esler et al., 2002; Edbauer et al., 2002), aph-1, and pen-2 (Francis et al., 2002). Although their respective roles in the regulation of γ-secretase activity have not yet been defined, loss of any of these components affects both APP and Notch processing. In contrast, as shown in the examples that follow, lithium does not inhibit Notch processing, indicating that lithium is not a general inhibitor of γ-secretase. While consensus sites for GSK-3 phosphorylation have been identified in PS1 that are important for PS1 stability, mutation of these sites does not affect γ-secretase activity (Kirschenbaum et al., *J. Biol. Chem.* 276:7366-7375 (2001)). Thus, it is unlikely that GSK-3α plays a role in the biogenesis, stability, or overall activity of the γ-secretase complex. Rather, GSK-3α appears to regulate γ-secretase activity toward specific substrates or access of these substrates to the γ-secretase complex.

Recently, a subset of non-steroidal anti-inflammatory drugs (NSAIDs) has also been shown to reduce $A\beta_{42}$ levels without affecting Notch cleavage (Weggen et al., *Nature* 414:212-216 (2001), see also U.S. Pat. No. 6,160,018 suggesting lithium as a possible counterions in the generation of an enantiomeric form of a NSAID for the treatment of Alzheimer's disease). While the target of these NSAIDs has not been determined in this context, the mechanisms of lithium and NSAIDs appear to differ, as NSAIDs shift γ-secretase cleavage of APP to increase $A\beta_{38}$ at the expense of $A\beta_{42}$, while lithium inhibits γ-secretase cleavage, reducing $A\beta_{40}$ and $A\beta_{42}$. This apparent difference in mechanism suggests that combination therapy of the lithium as used in the present invention with an NSAID could have an enhanced effect in reducing Aβ peptide accumulation, and also in the production of GSK-3α.

Both GSK-3α and GSK-3β phosphorylate tau protein, which is a microtubule-binding protein that, in its hyperphosphorylated state, is the major component of neurofibrillary tangles (Alvarez et al., *Bipolar Disord.* 4:153-165 (2002)). Lithium inhibits GSK-3 mediated tau phosphorylation (Phiel et al., 2001). However, that function is not the focus of the present treatment of Alzheimer's disease. Rather by focussing on GSK-3α as a target, the present use of a GSK-3α inhibitor, e.g., lithium, provides an unforeseen method for reducing the formation of amyloid plaques and neurofibrillary tangles, the two primary pathological features of Alzheimer's disease. Lithium has also been demonstrated to protect neurons from proapoptotic stimuli, and thus, may also reduce neuronal cell death associated with Alzheimer's (reviewed in Alvarez et al., 2002).

Lithium has been used for more than fifty years to treat bipolar disorder, but has a narrow therapeutic window and a higher frequency of side effects in older patients. Thus, while lithium might be considered to prevent progression of AD symptoms, especially in younger patients carrying FAD mutations or Down's syndrome patients, new agents that specifically target GSK-3α may prove valuable in the treatment of AD.

The brains of individuals with AD exhibit neuronal degeneration and characteristic lesions variously referred to as amyloidogenic plaques, vascular amyloid angiopathy, and neurofibrillary tangles. Large numbers of these lesions, particularly amyloidogenic plaques and neurofibrillary tangles, are generally found in several areas of the human brain important for memory and cognitive function in patients with AD. Smaller numbers of these lesions in a more restricted anatomical distribution are found in the brains of most aged humans who do not have clinical AD, as well as patients suffering from Down's Syndrome and Hereditary Cerebral Hemorrhage with Amyloidosis of the Dutch-Type.

The term "subject" is used interchangeably herein with "patient" and is intended to include living organisms in which Alzheimer's disease, or any recognized condition that may be related thereto, may develop, and in which lithium provides a treatment therefor in accordance with the present invention, e.g., preferably mammals, most preferably humans. Examples of subjects include humans, dogs, cats, mice, rats, and transgenic species thereof. For example, animals within the scope of the invention include animals of agricultural interest, such as livestock and fowl.

For practicing the methods of the invention, particularly in vivo, the lithium or lithium salt compositions and carriers therefor, are administered to the subjects in a biologically compatible form suitable for pharmaceutical administration in vivo. By "biologically compatible form suitable for administration in vivo" is meant, e.g., lithium or lithium salts prepared as described herein, to be administered in any circumstance in which any toxic effects are outweighed by the therapeutic effects of the treatment. Also included are compositions, such as lithium, that act intracellularly to inhibit or reduce levels of a subject's formation of amyloid plaques and neurofibrillary tangles or accumulation of Aβ peptide levels, particularly $A\beta_{40}$ and $A\beta_{42}$ peptides, or GSK-3α levels, or the production or processing of APP. Moreover, as will be understood by those skilled in the art, "bioavailable" or "biocompatible," as used herein, means that a particular element or compound such as lithium is, for example by its particular oxidation state or the components with which it is complexed, in a form which allows for the element or compound to be absorbed, incorporated or be otherwise physiologically available to the individual to whom it is administered. Any bioavailable sources are contemplated for use in the practice of the present invention. When lithium is administered to a subject, lithium salts are preferred.

The methods are also useful for research purposes, wherein GSK-3 inhibitors, such as lithium or any other GSK-3 inhibitor, and carriers therefor are administered to brain tissue or cells of any species in vitro. Such treated cells or tissues may also be returned to the subject or another subject of any species, in which case the applications are acceptably used ex vivo.

Also embodied in the invention are methods of treating a GSK-3α-related disorder in an animal, wherein the methods comprise administering to the animal (or to the brain, brains cells or brain tissue of an animal) a GSK-3α inhibitor suspended in a pharmaceutically acceptable carrier. The GSK-3α related disorder, which is treated according to the method of the invention, may be any disorder mediated by GSK-3α activity, but is preferably Alzheimer's disease.

Thus, the invention is a method for treating a biological condition mediated by GSK-3α activity by administering an effective amount of a pharmaceutical composition comprising a selective GSK-3α inhibitor to a subject having a condition mediated by GSK-3α activity or susceptible to such a condition, e.g., Alzheimer's disease. The selective inhibitor of GSK-3α activity, includes lithium, or a pharmaceutically acceptable salt thereof, and a physiologically acceptable carrier.

The invention is also embodied by an in vitro method of identifying an inhibitor of GSK-3α kinase activity, and includes a pharmaceutical composition comprising an inhibitor identified by this in vitro method.

In yet another embodiment, the invention provides methods for the treatment of a subject having Alzheimer's disease, wherein the methods comprise administering to the subject (or to the brains cells or tissue thereof) an effective amount of an inhibitor of GSK-3, such as lithium, specifically to reduce processing of amyloid precursor proteins to beta-amyloid (Aβ) peptides, and thus to prevent, inhibit or reverse Alzheimer's disease. Moreover, this effect of lithium is mediated through the inhibition of GSK-3α. Because the α isoform of GSK-3 (GSK-3α) has been found herein to be specifically responsible for APP processing, in another embodiment of this invention, agents that specifically target GSK-3α are especially useful in the treatment, prevention, and possible reversal of Alzheimer's disease. Further provided are methods for treating a condition mediated by GSK-3α activity by administering a selective inhibitor of GSK-3α, which is preferably a therapeutically effective amount of a composition that specifically inhibits GSK-3α, but does not inhibit or block GSK-3β or other lithium sensitive enzymes. In an embodiment of the invention there are provided one or more bioavailable sources of the GSK-3α) inhibitor, such as lithium, or a pharmaceutically acceptable salt thereof, and a physiologically acceptable carrier.

Also embodied are methods for treating in a subject Alzheimer's disease, or the conditions relating thereto, wherein the methods comprise administering to the subject (or to the brains cells or tissue thereof) an Alzheimer's disease-reducing or disease-inhibiting amount of an inhibitor of GSK-3, such as lithium, and a physiologically acceptable carrier. Also provided are methods for treating, inhibiting or reducing Alzheimer's disease related conditions, such as the formation of amyloid plaques and neurofibrillary tangles or accumulation of Aβ peptides (particularly $A\beta_{40}$ and $A\beta_{42}$ peptides) in the brain or in brain cells or tissue, as well as methods for preventing or inhibiting the γ-secretase cleavage of APP in the brain.

In yet another embodiment of the invention, there are further provided methods for stabilizing a subject susceptible to Alzheimer's disease or the formation of amyloid plaques and neurofibrillary tangles or accumulated Aβ peptides (particularly $A\beta_{40}$ and $A\beta_{42}$ peptides) in the brain, thereby also stopping or inhibiting the γ-secretase cleavage of APP, wherein the methods comprise administering to the subject (or to the brains cells or tissue thereof) a stabilizing amount of an inhibitor of GSK-3, such as lithium, and a physiologically acceptable carrier.

In yet another embodiment, there are provided methods for treating a subject susceptible to Alzheimer's disease or the formation of amyloid plaques and neurofibrillary tangles or accumulated Aβ peptides (particularly $A\beta_{40}$ and $A\beta_{42}$ peptides) in the brain, thereby also preventing the γ-secretase cleavage of APP in the brain, wherein the methods comprise administering to a subject (or to the brains cells or tissue thereof) a preventing amount of an inhibitor of GSK-3, such as lithium, and a physiologically acceptable carrier.

Also embodied in the invention is a composition that inhibits GSK-3α activity in vivo, such as a pharmaceutically acceptable lithium composition. All combinations, sources and amounts of the active ingredients discussed herein in conjunction with the compositions of the present invention are also contemplated as being administered in accordance with the foregoing methods.

The invention also is embodied by a kit for inhibiting glycogen synthase kinase 3α activity, preferably in vivo. The kit comprises the GSK-3α activity-inhibiting composition described above, such as lithium, and an instructional material. The instructional material can, for example, be one selected from the group consisting of an instructional material that describes administration of the composition to an animal in order to inhibit GSK-3α activity, or an instructional material that describes administration of the composition to an animal in order to alleviate a disorder known to be alleviated by administration of the GSK-3α inhibitor, such as lithium.

Preferably the foregoing methods further comprise monitoring such subject's Aβ peptide levels, particularly $A\beta_{40}$ and $A\beta_{42}$ peptides, or GSK-3α levels, or the γ-secretase cleavage of APP.

Administration of an "effective amount" or a "therapeutically effective amount" of a GSK-3 inhibitor or GSK-3α inhibitor, respectively, of the present invention is defined as an amount that is useful, at dosages and for periods of time necessary to achieve the desired result. For example, a therapeutically effective amount of a GSK-3 inhibitor or GSK-3α inhibitor (also referred to as a "therapeutically effective inhibitor composition") in accordance with the present invention may vary according to factors, such as the disease state, age, sex, and weight of the subject, and the ability of the agent to elicit a desired response particularly to Alzheimer's disease in the subject. Dosage regimens of a GSK-3 inhibitor or GSK-3α inhibitor, such as lithium, in the patient may be adjusted to provide the optimum therapeutic response. For example, several divided doses may be administered daily or the dose may be proportionally reduced as indicated by the exigencies of the therapeutic situation. "Pharmaceutically acceptable GSK-3 inhibitor compositions," or "pharmaceutically acceptable GSK-3α inhibitor compositions," "pharmaceutical inhibitor compositions" or simply "pharmaceutical compositions" contemplated for use in the practice of the present invention (such as those comprising a GSK-3 inhibitor or GSK-3α inhibitor, respectively) refer to those compositions that are not harmful to a subject when administered in vivo, and which when administered in therapeutically effective amounts or concentrations are sufficient to inhibit, block, or even reverse, Aβ peptide accumulation or undesirable APP processing, respectively. "Pharmaceutically acceptable lithium salt(s)," refer to lithium salts prepared from pharmaceutically acceptable, non-toxic acids or bases. The active compounds contemplated for use herein, include pharmaceutical compositions or other compounds in an amount sufficient to produce the desired preventive, inhibitory or reversing effect upon Alzheimer's disease, or processes or conditions related thereto, or to inhibit or block Aβ peptide accumulation or GSK-3α activity relating to γ-secretase cleavage of APP. The administration to the patient of such compositions can be in the form of a solid, a solution, an emulsion, a dispersion, a micelle, a liposome, and the like, wherein the resulting GSK-3 inhibitor composition contains one or more of the active compounds contemplated for use herein, as active ingredients thereof, in admixture with an organic or inorganic carrier or excipient suitable for nasal, enteral, oral, inhalation, or transdermal applications (see, e.g., U.S. Pat. Nos. 6,375,990 or 6,335,034), or parenteral applications, or osmotic pump, or vaginal, rectal or ophthalmic administration, for example, as such methods may already be administered in the treatment of depression.

The term "pharmaceutically acceptable carrier" means a chemical composition with which a pharmaceutically active agent can be combined and which, following the combination, can be used to administer the agent to a subject (e.g., a mammal, such as a human). The term "physiologically acceptable" ester or salt means an ester or salt form of a pharmaceutically active agent which is compatible with any other ingredients of the pharmaceutical composition and which is not deleterious to the subject to which the composition is to be administered. In the active GSK-3 inhibitor, such as lithium, ingredients may be compounded, for example, with the usual non-toxic, pharmaceutically and physiologically acceptable carriers for tablets, pellets, capsules, troches, lozenges, aqueous or oily suspensions, dispersible powders or granules, suppositories, solutions, emulsions, suspensions, hard or soft capsules, caplets or syrups or elixirs and any other form suitable for use.

Oral administration is a preferred route of administration of the GSK-3 inhibitor, such as lithium composition, or GSK-3α activity-inhibiting or -blocking composition of the present invention. A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture.

In addition, such compositions may contain one or more agents selected from flavoring agents (such as peppermint, oil of wintergreen or cherry) to create an acceptable or a pleasant taste for optimal patient compliance, coloring agents, preserving agents, and the like, in order to provide pharmaceutically elegant and palatable preparations.

The carriers that can be used include, e.g., glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents may be used.

Tablets containing the active ingredients in admixture with non-toxic pharmaceutically acceptable excipients may also be manufactured by known methods. Pharmaceutically acceptable excipients used in the manufacture of tablets include, but are not limited to, inert diluents, granulating and disintegrating agents, binding agents, and lubricating agents. The excipients used may be, for example, (1) inert diluents, such as calcium carbonate, lactose, calcium phosphate, sodium phosphate, and the like; (2) granulating and disintegrating agents, such as corn starch, potato starch, alginic acid, and the like; (3) binding agents, such as gum tragacanth, corn starch, gelatin, acacia, and the like; and (4) lubricating agents, such as magnesium stearate, stearic acid, talc, and the like.

Known dispersing agents include, but are not limited to, potato starch and sodium starch glycolate. Known surface active agents include, but are not limited to, sodium lauryl sulfate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

The tablets may be uncoated, or they may be preferably coated by known techniques to delay disintegration and absorption in the gastrointestinal tract, thereby providing sustained action over a longer period. For example, a time delay material, such as glyceryl monostearate or glyceryl distearate may be employed. The tablets may also be coated by the techniques described in the U.S. Pat. Nos. 4,256,108; 4,160,452; and 4,265,874, to form osmotic therapeutic tablets for controlled release.

Oral compositions may be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., *Aliment. Pharmacol. Therap.* 1:273-280 (1987)). Polymers capable of providing site-specific colonic delivery can also be used, wherein the polymer relies on the bacterial flora of the large bowel to provide enzymatic degradation of the polymer coat, and hence, release of the drug.

When formulations for oral use are in the form of hard gelatin capsules, the active ingredients may be mixed with an inert solid diluent, for example, calcium carbonate, calcium phosphate, kaolin, or the like (see, e.g., U.S. Pat. No. 6,517,859). They may also be in the form of soft gelatin capsules, wherein the active ingredients are mixed with water or an oil medium, for example, peanut oil, liquid paraffin, olive oil and the like.

Pulsed release technology, such as that described in U.S. Pat. No. 4,777,049, may also be used to administer the active agent to a specific location within the gastrointestinal tract. Such systems permit drug delivery at a predetermined time and can be used to deliver the active agent, optionally together with other additives that my alter the local microenvironment to promote agent stability and uptake, directly to the colon, without relying on external conditions other than the presence of water to provide in vivo release.

Liquid formulations of a pharmaceutical composition of the invention which are suitable for oral administration may be prepared, packaged, and sold either in liquid form or in the form of a dry product intended for reconstitution with water or another suitable vehicle prior to use.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intravenous, intraarterial, intramuscular, or intrastemal injection and intravenous, intraarterial, or kidney dialytic infusion techniques.

The pharmaceutical compositions may also be in the form of a sterile injectable suspension. Such a suspension may be formulated according to known methods, using sterile aqueous solutions (where water soluble) or dispersions and sterile powders for the extemporaneous preparation of sterile injectable solutions or dispersion. Suitable dispersing or wetting agents and suspending agents may be used. The composition must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The sterile injectable preparation may also be a sterile injectable solution or suspension in a non-toxic parenterally-acceptable diluent or solvent, for example, as a solution in 1,4-butanediol. Sterile, fixed oils are conventionally employed as a solvent or suspending medium. For this purpose, any bland fixed oil may be employed including synthetic mono- or diglycerides, fatty acids (including oleic acid), polyunsaturated fatty acids (such as dihomo-gamma-linolenic acid, gamma-linolenic acid and linoleic acid), naturally occurring vegetable oils or synthetic fatty vehicles like ethyl oleate or the like (see, e.g., U.S. Pat. No. 5,252,333 teaching pharmaceutical compositions containing lithium salts of $C_{18-22}$ polyunsaturated fatty acids adapted for the treatment of Alzheimer's disease). Prolonged absorption of the injectable compositions can be brought about by including in the composition an agent that delays absorption, for example, aluminum monostearate or gelatin. Buffers, preservatives, antioxidants, and the like can be incorporated as required.

Formulations suitable for topical administration include, but are not limited to, liquid or semi-liquid preparations, such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles, wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulizing or atomizing device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmically-administrable formulations include those comprising the active ingredient in microcrystalline form or in a liposomal preparation.

A pharmaceutical composition of the invention may be prepared, packaged, or sold in a formulation suitable for vaginal administration. Such a composition may be in the form of, for example, a suppository, an impregnated or coated vaginally-insertable material, such as a tampon, a douche preparation, or a solution for vaginal irrigation. Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying. Douche preparations or solutions for vaginal irrigation may be made by combining the active ingredient with a pharmaceutically acceptable liquid carrier. As is well known in the art, such preparations may be administered using, and may be packaged within, a delivery device adapted to the vaginal anatomy of the subject. Such preparations may further comprise various additional ingredients including, but not limited to, antioxidants, antibiotics, antifungal agents, and preservatives.

A pharmaceutical composition of the invention may be prepared, packaged, or sold in a formulation suitable for rectal administration. Such a composition may be in the form of, for example, a suppository, a retention enema preparation, and a solution for rectal or colonic irrigation. These compositions may be prepared by mixing the active ingredients with a suitable non-irritating excipient, such as cocoa butter, synthetic glyceride esters of polyethylene glycols (which are solid at ordinary temperatures, but which liquefy and/or dissolve in the rectal cavity to release the active ingredients), and the like.

In addition, sustained release systems, including semipermeable polymer matrices in the form of shaped articles (e.g., films or microcapsules) can also be used for the administration of the active compound employed herein.

As will be appreciated by those of skill in the art, Alzheimer's disease presents a complicated array of conditions and symptoms. Because of the inter-relatedness of these conditions and symptoms, invention compositions are useful in treating many of them. In addition, there are a number of precursor conditions which portend the development of Alzheimer's disease and which can be treated by administration of compositions as described herein. Therefore, in accordance with another aspect of the present invention, there are provided methods of using GSK-3 inhibitors, such as lithium or other such inhibitors, for reducing or minimizing in the brain or brain tissue the formation of amyloid plaques and neurofibrillary tangles or accumulated Aβ peptides, for blocking or inhibiting production of $A\beta_{40}$ and $A\beta_{42}$ peptides by interfering with γ-secretase cleavage of APP, and for specifically blocking or inhibiting GSK-3α activity, which is specifically required for maximal processing of APP, thereby reducing the dosage of other anti-Alzheimer's disease agents that the subject may be taking. Thus, the general well-being of the Alzheimer's disease patient is in general improved, wherein the methods comprise administration of compositions as described herein.

Since individual subjects may present a wide variation in severity of symptoms and each active ingredient has its unique therapeutic characteristics, it is up to the practitioner to determine a subject's response to treatment and vary the dosages of the active ingredients accordingly. It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the composition or salt prepared in accordance with the present invention and the particular therapeutic effect to be achieved.

A pharmaceutical composition of the invention may be administered to deliver a dose of between 500 picograms per kilogram body weight per day and 1 milligrams per kilogram body weight per day to a subject. However, lithium should generally not be administered to patients having significant renal or cardiovascular disease, severe debilitation or dehydration, sodium depletion, or to patients receiving diuretics, since the risk of lithium toxicity can be high in such patients. (*Physicians Desk Reference*, (1997) pp. 2352), as are numerous other side effects (detailed in the *Physicians Desk Reference* (1997) pp. 2352, 2658), although the mechanism(s) by which lithium exerts these diverse effects are unclear.

It is understood that the ordinarily skilled physician or veterinarian will readily determine and prescribe an effective amount of the compound to alleviate a disorder associated with aberrant GSK-3α activity in the subject. In so proceeding, the physician or veterinarian may, for example, prescribe a relatively low dose at first, subsequently increasing the dose until an appropriate response is obtained. It is further understood, however, that the specific dose level for any particular subject will depend upon a variety of factors including the activity of the specific compound employed, the age, body weight, general health, gender, and diet of the subject, the time of administration, the route of administration, the rate of excretion, any drug combination, and the severity of the disorder being treated. Since lithium compounds have be well-tested in the treatment of human patients suffering from depression, dosage amounts and safety concerns are already known, or can be readily determined, without undue experimentation by those skilled in the art of treating patients (see also Phiel et al., 2001; U.S. Pat. No. 4,556,068).

As used herein, "additional ingredients" include, but are not limited to, one or more of the following: excipients;

surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient. A unit dose of a pharmaceutical composition of the invention generally comprises from about 1 nanogram to about 1 gram of the active ingredient, and preferably comprises from about 50 nanograms to about 10 milligrams of the active ingredient.

In addition to the active GSK-3 inhibitor or GSK-3α-specific inhibitor component, a pharmaceutical composition of the invention may further comprise one or more additional pharmaceutically active agents. Particularly contemplated additional agents include virus particles comprising one or more polypeptides or polynucleotide(s) encoding such a polypeptide. The polypeptides can also be administered as fusion proteins, such as proteins that would facilitate entry into cells.

Another embodiment of the invention relates to a kit comprising a pharmaceutical composition of the invention and an instructional material. As used herein, an "instructional material" includes a publication, a recording, a diagram, or any other medium of expression used to communicate the usefulness of the pharmaceutical composition of the invention for inhibiting GSK-3 or GSK-3α-specific activity in a subject. The instructional material may also, for example, describe an appropriate dose of the pharmaceutical composition of the invention. The instructional material of the kit of the invention may, for example, be affixed to a container containing a pharmaceutical composition of the invention or be shipped together with a container containing the pharmaceutical composition. Alternatively, the instructional material may be shipped separately from the container with the intention that the instructional material and the pharmaceutical composition be used cooperatively by the recipient.

The invention is further embodied by a kit comprising a pharmaceutical composition of the invention and a delivery device for delivering the GSK-3α inhibiting composition to a subject. By way of example, the delivery device may be a squeezable spray bottle, a metered-dose spray bottle, an aerosol spray device, an atomizer, a dry powder delivery device, a self-propelling solvent/powder-dispensing device, a syringe, a needle, a tampon, or a dosage-measuring container. The kit may further comprise an instructional material as described herein.

The invention includes transgenic (preferably non-human) animals, which comprise a transgene encoding a polypeptide GSK-3α inhibiting composition described in this disclosure. The polypeptide is able to interact with GSK-3α, and inhibit GSK-3α activity, thereby preventing or inhibiting normal tau phosphorylation associated with GSK-3α. Thus, expression of the transgene can mimic the effect of GSK-3 inhibitor administration in the animal. The transgene preferably comprises a promoter from which initiation of transcription can be controlled. Numerous examples of controllable promoters are known in the art, and include inducible promoters, repressible promoters, temperature-sensitive promoters, and tissue-specific promoters. A preferred promoter is the calcium-calmodulin dependent protein kinase II alpha (CaMKIIalpha) promoter. Expression of polypeptide s operably linked with this promoter sequence is generally limited to adult neurons of the forebrain, including neurons of the neocortex, the hypothalamus, the amygdala, and the basal ganglia. The transgenic animal can be of any species for which transgenic generation methods are known (i.e., including at least mammals such as cows, goats, pigs, sheep, and rodents such as rats and mice).

The present invention is further described by example. These examples are provided for purposes of illustration only, and are not intended to be limiting unless otherwise specified. The various scenarios are relevant for many practical situations, and are intended to be merely exemplary to those skilled in the art. These examples are not to be construed as limiting the scope of the appended claims, rather such claims should be construed to encompass any and all variations that become evident as a result of the teachings provided herein.

EXAMPLES

Example 1

Role of GSK-3 and Effect of Lithium on Production of $A\beta_{40}$ and $A\beta_{42}$ Peptides.

To investigate the role of GSK-3 in the production of peptides $A\beta_{40}$ and $A\beta_{42}$, Chinese hamster ovary (CHO) cells stably expressing APP (CHO-APP$_{695}$) were treated with lithium chloride (LiCl), which is a direct inhibitor of GSK-3α and β (Phiel et al., 2001). CHO$_{695}$ cells (available commercially, e.g., American Type Culture Collection (ATCC), Manassas, Va.) were maintained in culture in MEMα+5% fetal bovine serum (FBS) (e.g., BioWhittaker, Walkersville, Md.) with added penicillin/streptomycin and glutamine. Stocks of lithium chloride were prepared in sterile water. To quantify the $A\beta_{40}$ and $A\beta_{42}$ secretion following treatment with LiCl, the CHO-APP$_{695}$ cells were plated in 6-well dishes at a density of $5\times10^5$ cells per well. LiCl was added to the cells in fresh medium, and media and cells were collected 24 hours later. Aβ determinations from the media were made by sandwich ELISA in femtomoles using the method of Suzuki et al., *Science* 264:1336-1340 (1994).

Notably, although CHO cells were used, one is not limited to such cells. CHO cells are acceptable models for human cellular responses (Sahasrabudhe et al., *J. Biol. Cell* 267: 25602-25608 (1992)). For example, human cells overexpressing APP (293Ts for example) could be used. In fact, it is shown herein that lithium reduces Aβ levels in neurons derived from human embryonic carcinoma cells (NTera2/D1 or NT2 cell line from which mouse and human primary neurons were derived). $CHO_{695}$ cells were chosen because they were readily available and generate Aβ peptides at levels that are sufficient for the detection methods used.

To visualize the APP fragments, $CHO_{695}$ cells plated on 6-well dishes were methionine-deprived for 30 minutes by incubation in methionine-free DMEM (Life Technologies, Inc., Grand Island, N.Y.) before adding 500 µCi $^{35}$S-methionine (Perkin Elmer Life Sciences, Inc., Boston Mass.) per ml of DMEM with 5% dialyzed FBS (Invitrogen) and mg/ml L-proline for 2.5 hours. Medium was collected and cells (2 wells/sample) were rinsed twice with PBS (phosphate buffered saline), then scraped into RIPA buffer (a standard immunoprecipitation buffer, see, Harlow and Lane (eds.), In Antibodies: a laboratory manual, Cold Spring Harbor Laboratory Press, NY (1988)). Lysates were sonicated and centrifuged at 100,000×g for 20 minutes. Using protein A/G agarose beads (Santa Cruz Biotechnologies, Santa Cruz, Calif.), media was immunoprecipitated with the antibody BAN-50 (Suzuki et al., 1994) that recognizes Aβ amino acids 1-10, and cell lysates were immunoprecipitated with antibody 2493 (Lee et al., *J. Biol. Chem.* 278:4458-2466 (2003)), which is a rabbit polyclonal antibody that recognizes the C-terminus of APP. Proteins were resolved by electrophoresis on 10/16% step gradient Tris-tricine polyacrylamide gels. Gels were fixed in 50% methanol+5% glycerol, dried, and exposed to a PhosphorImager screen.

For comparison purposes, the results were normalized to levels of intracellular full-length APP. APP levels were quantified by SDS-PAGE followed by western immunoblotting with the amino-terminal APP antibody Karen (Turner et al., *J. Biol. Chem.* 271:8966-8970 (1996)), and visualized using $^{125}$I-labelled secondary antibodies by PhosphorImager analysis and ImageQuant software (Amersham Biosciences Corp, Piscataway, N.J.).

LiCl robustly inhibited production of both $A\beta_{40}$ and $A\beta_{42}$, with an $IC_{50}$ between 1-2 mM, well within the therapeutic range of lithium for bipolar disorder. Meanwhile, sodium chloride (NaCl) was found to have no effect on APP processing (FIG. 1a), which is consistent with a recent report using transient overexpression of the APP carboxyl terminus C100 in COS7 cells (Sun et al., *Neurosci. Lett.* 321:61-64 (2002)).

Example 2

Lithium Inhibits $A\beta_{40}$ and $A\beta_{42}$ Production at the Level of γ-secretase.

To confirm the effect of lithium on the level of APP peptides, the accumulation of APP processing intermediates was measured in the presence of LiCl. The cleavage of APP by α or β-secretase generates APP C terminal fragments (CTFs), which are then further cleaved by γ-secretase. If γ-secretase is inhibited, for example with a known inhibitor of γ-secretase activity, DFK-167, then APP CTFs accumulate (see, Wolfe et al., 1999).

The reduction of Aβ was confirmed by the metabolic $^{35}$S-methionine labeling of $CHO-APP_{695}$ cells in either the presence or absence of LiCl. $CHO-APP_{695}$ cells were maintained, cultured and visualized as described in Example 1, as were the LiCl treatments. Stocks of the γ-secretase inhibitor, DFK-167 (Enzyme Systems Products, Livermore, Calif.) were prepared in DMSO (see, Wolfe et al., *J. Med. Chem.* 41:6-9 (1998)).

Figure 1B:
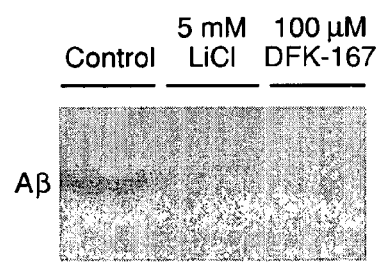

$CHO-APP_{695}$ cells were treated with 5 mM LiCl or with the, 100 µM DFK-167 for 24 hours. At the end of the 24 hour exposure, the APP fragments were $^{35}$S-methionine labeled and treated as in Example 1. The labeled Aβ secreted from $CHO-APP_{695}$ cells was immunoprecipitated from the medium, then SDS-PAGE separated and PhosphorImager visualized. Control cells were similarly handled, but without treatment with LiCl or DFK-167. Both LiCl and DFK-167 were found to dramatically reduce the steady-state levels of secreted Aβ peptides (see, FIG. 1b, lanes 2 and 3 respectively).

Accordingly, lithium did not affect steady-state levels of APP (FIG. 1c) or the levels of the N-and C-terminal fragments of PS1 (data not shown), nor did it interfere with the detection of Aβ peptides (not shown). Lithium, therefore, functionally reduced the level of Aβ peptides, apparently at a post-translational step, such as APP processing or Aβ stability.

To confirm that lithium inhibits $A\beta_{40}$ and $A\beta_{42}$ production at the level of γ-secretase, CHO-APP695 cells were treated, as above, with 5 mM LiCl or 100 µM DFK-167 for 24 hours. The intracellular APP from the $CHO-APP_{695}$ cells was immunoprecipitated from the medium, then SDS-PAGE separated. APP holoprotein and APP C-terminal fragments (C99, C89, and C83) were PhosphorImager visualized (see, FIG. 1c).

Figure 1C:
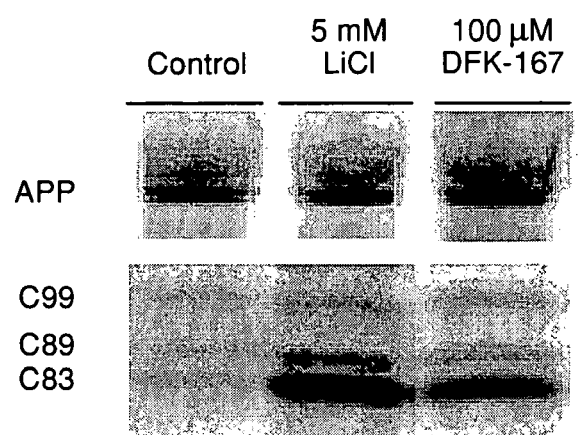

As shown in FIG. 1c, exposure of $CHO-APP_{695}$ cells to lithium for 24 hours caused an accumulation of APP CTFs similar to the effect shown as a result of treatment with DFK-167. Thus, the accumulation of the APP CTFs demonstrates that lithium inhibits $A\beta_{40}$ and $A\beta_{42}$ production at the level of γ-secretase.

Example 3

Lithium is Neither an Inhibitor of Notch Processing or γ-secretase.

The γ-secretase activity is also required for the release of the Notch intracellular domain (NICD) (De Strooper et al., *Nature* 398:518-522 (1999)). Since lithium inhibits APP processing at the level of γ-secretase, the effects of lithium were examined on Notch processing. ΔE-Notch has been constructed to lack most of its extracellular domain, but it retains the transmembrane domain containing the γ-secretase cleavage site. Thus, it is constitutively cleaved (Schroeter et al., *Nature* 393:382-386 (1998)).

Figure 1D:
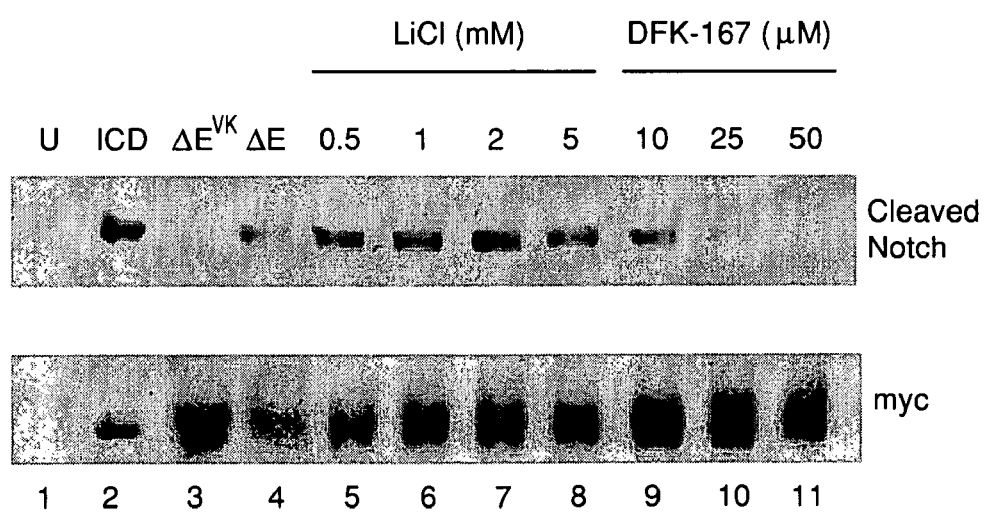

$CHO-APP_{695}$ cells were plated at a density of $1 \times 10^5$ cells per well of 6-well dishes. Cells were transfected with 2 µg of either Notch-ICV or Notch-ΔE as indicated in FIG. 1d, see lanes 4-11. Notch ΔE in pCS2MT and Notch ICV in pCS2MT were kindly provided by R. Kopan (published construct). Notch ΔE V1744K in pCS2MT was created by site-directed mutagenesis using a Quikchange™ mutagenesis kit (Stratagene, La Jolla, Calif.) and confirmed by sequencing APP-WT and APP-Swedish (KM670/671NL) in pSFV as described previously (Fonnan et al., *J. Biol. Chem.* 272:32247-32253 (1997)).

Twenty four (24) hours later, media was changed and drugs were added—either lithium (ranging 0.5 mM to 5 mM LiCl) or DFK-167 (ranging 10 µM to 50 µM) and allowed o remain for 24 hours. After exposure to the drugs, the cells were harvested as described above, and immunoblotted with either increasing concentrations of myc (9E10) antibody or cleaved Notch antibody that recognizes the cleavage product (Cell Signaling Technologies, Beverly, Mass.) (see concentrations shown in FIG. 1d). The myc 9E10 antibody only recognizes Notch 1 processed at the γ-secretase cleavage site (between residues 1743-1744 in full-length Notch). Notch intracellular domain (NICD), beginning at residue 1744 of full-length Notch, was used as a positive control for cleavage (FIG. 1d, lane 2). ΔE-Notch V1744K (see, Schroeter et al., 1998) has a point mutation in the γ-secretase cleavage site of ΔE-Notch, and accordingly was used as a negative control for cleavage (FIG. 1d, lane 3). All Notch constructs had a C-terminal myc tag. Neither the overexpression of GSK-3α or GSK-3β had any effect on Notch cleavage (data not shown).

Lithium at the studied concentrations did not inhibit Notch processing as assessed by western blotting. ΔE-V1744K was not processed because of the point mutation at the γ-secretase cleavage site, and therefore, is not detected with the antibody specific for cleaved Notch (FIG. 1d, lane 3). Thus, lithium was shown not to be a general inhibitor of γ-secretase under these conditions.

Example 4

Lithium Reduces Aβ Production Because It Inhibits GSK-3.

While lithium is a direct and highly selective inhibitor of GSK-3 (Phiel et al., Annu. Rev. Pharmacol. Toxicol. 41:789-813 (2001)), it also inhibits inositol monophosphatase (IMPase), as well as structurally related phosphomonoesterases, and phosphoglucomutase (Phiel et al., 2001). To confirm that lithium reduces Aβ production through inhibition of GSK-3, rather than a reduction resulting from inhibition of IMPase, or the structurally related phosphomonoesterases or phosphoglucomutase, the CHO-APP$_{695}$ cells were treated with the structurally unrelated GSK-3 inhibitor, kenpaullone (Leost et al., Eur. J. Biochem. 267:5983-5994 (2001)).

Figure 2A:
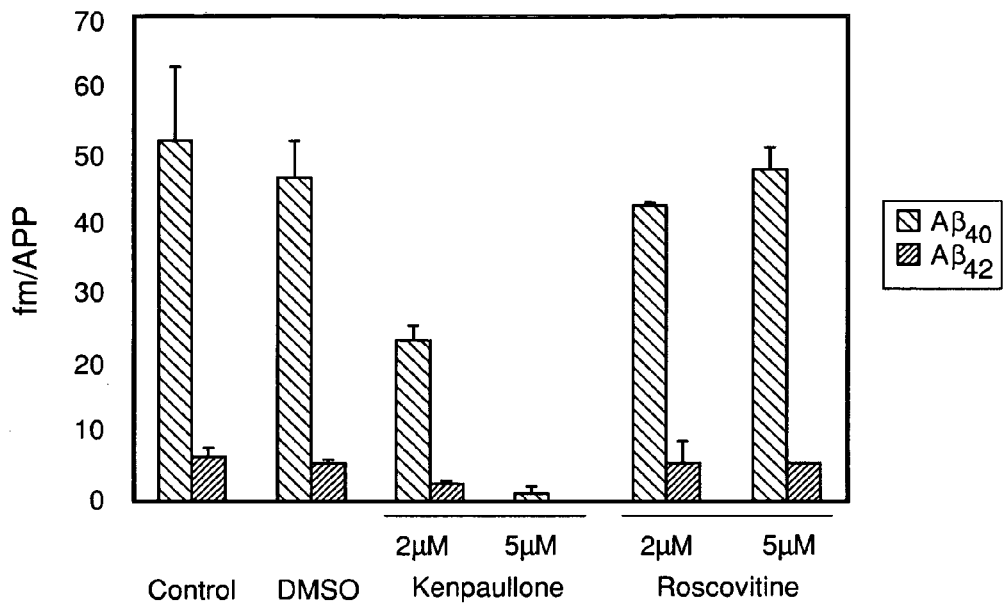
FIGS. 2a-2d show that GSK-3 inhibitors reduce Aβ, independent of β-catenin stabilization.

Stocks of kenpaullone (Calbiochem, La Jolla, Calif.) were prepared in DMSO. Secreted labeled Aβ secreted from CHO-APP$_{695}$ cells was obtained as described in the preceding examples. Drugs were added to fresh medium, and medium and cells were collected, as described above, 24 hours later. Immunoprecipitates from the medium were SDS-PAGE separated and PhosphorImager visualized. As shown in FIG. 2a, kenpaullone (tested at concentrations of 2.0 µM and 5.0 µM, respectively) dramatically reduced both Aβ$_{40}$ and Aβ$_{42}$ secretion, resulting in a 50% reduction at 2.0 µM kenpaullone. At 5.0 µM, kenpaullone caused a reduction of greater than 90%.

However, kenpaullone is also known to inhibit cyclin-dependent kinases (cdks), although such inhibition requires at least 20-fold higher concentrations in vitro than the concentration needed for inhibition of GSK-3 (Leost et al., 2001). Nevertheless, to confirm that the effect seen was actually caused by the lithium and not by a reaction with another composition, CHO-APP$_{695}$ cells were treated with roscovitine, a cdk inhibitor that does not inhibit GSK-3 (Leclerc et al., J. Biol. Chem. 276:251-260 (2001)). Stocks of roscovitine (Calbiochem) were prepared in DMSO. As expected, the roscovitine (tested at concentrations of 2.0 µM and 5.0 µM, respectively) had no effect on Aβ$_{40}$ and Aβ$_{42}$, as shown in FIG. 2a. Thus, neither kenpaullone nor roscovitine inhibited Aβ production through inhibition of cdks.

Figure 2B:
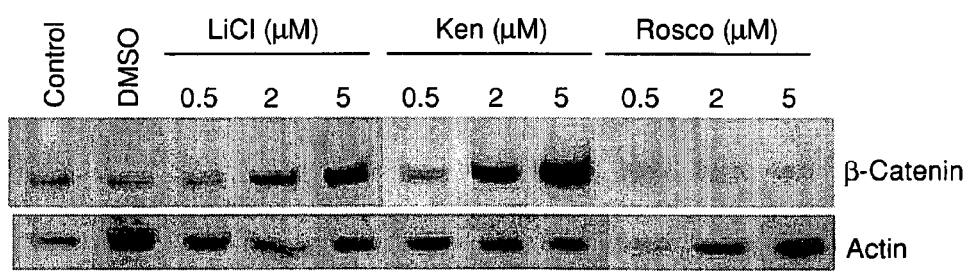

Inhibition of GSK-3 also causes accumulation of β-catenin protein. This was confirmed by western blot, in CHO-APP$_{695}$ cells treated with kenpaullone (tested at concentrations of 0.5 µM, 2.0 µM and 5.0 µM, respectively) or lithium (0.5 mM, 2.0 mM and 5.0 mM LiCl) as shown in FIG. 2b. Roscovitine was added as a control (tested at concentrations of 0.5 µM, 2.0 µM and 5.0 µM, respectively) in FIG. 2b, as had been in the study summarized in FIG. 2a. A western blot for actin is was used as a loading control (see FIG. 2b).

Example 5

Effect of Increasing β-catenin Protein on PS1 and Aβ$_{40}$ and Aβ$_{42}$ Production.

PS1 also interacts with β-catenin and has been shown to regulate β-catenin protein levels (Zhang et al., Nature 395:698-702 (1998)) and subcellular localization (Kang et al., 2002). Because GSK-3 inhibitors such as lithium and kenpaullone cause accumulation of β-catenin protein (Phiel et al., 2001), it is technically possible that β-catenin could play a role as either a downstream effector of PS1 or a direct modulator of PS1 function. Therefore, tests were conducted to determine whether increasing β-catenin protein could mimic the effect of lithium and kenpaullone on Aβ$_{40}$ and Aβ$_{42}$ production.

Figure 2C:
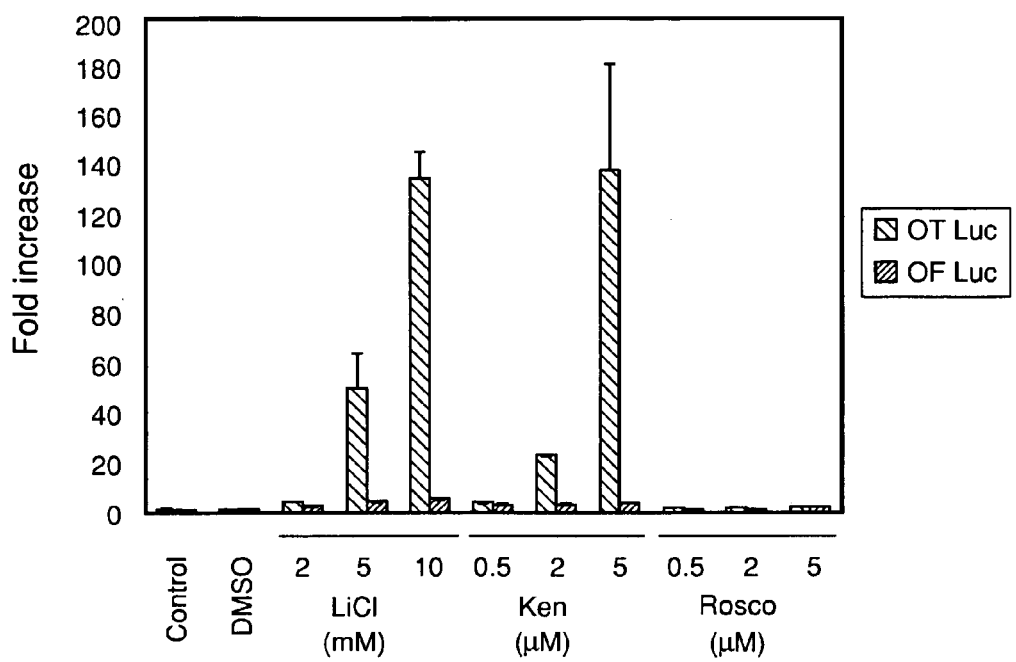

CHO-APP$_{695}$ cells were transfected with a β-catenin-responsive reporter construct, OT-luciferase (OT-Luc) (shown in FIG. 2c as light bars), or a mutated reporter, OF-luciferase (OF-Luc) (shown in FIG. 2c as dark bars). OT-luciferase was provided by K. Kinzler and B Vogelstein.

After transfection, cells were treated with lithium (at concentrations of 0.5 mM, 2.0 mM and 5 mM LiCl, respectively), kenpaullone (at concentrations of 0.5 mM, 2.0 mM and 5 mM, respectively) or roscovitine (at concentrations of 0.5 mM, 2.0 mM and 5 mM) for 24 hours. Cells were harvested and luciferase assays performed.

From the assays, it is clear that both kenpaullone and lithium inhibited GSK-3 in the CHO-APP$_{695}$ cells, as indicated by an accumulation of β-catenin protein (FIG. 2b; see Example 4), and by the activation of a β-catenin/Tcf-dependent reporter, Lef-OT (FIG. 2c).

Figure 2D:
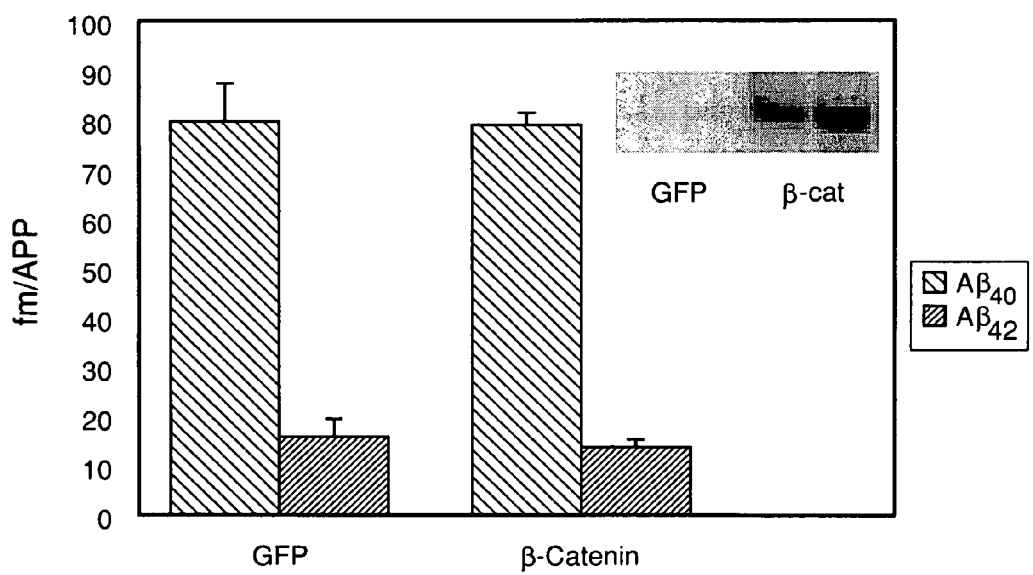

Xenopus β-catenin (Fagatto et al., J. Cell. Biol. 132:1105-1114 (1996)) was subcloned from plasmid pCS2+ into plasmid pSFV. Secreted Aβ$_{40}$ (FIG. 2d, light bars) and Aβ$_{42}$ (FIG. 2d, dark bars) levels were assessed as described in the preceding Examples, and as shown in FIG. 1. The FIG. 2d inset shows a western blot of endogenous green fluorescent protein (GFP) and overexpressed (β-cat) β-catenin in duplicate lanes. Overexpression of β-catenin did not affect Aβ production (FIG. 2d) under conditions that activated the β-catenin dependent reporter Lef-OT (OT-luciferase)(data not shown).

Semliki Forest Virus (SFV) vectors were also utilized to overexpress β-catenin and APP. SFV was prepared and titered in BHK cells (as previously described by Cook et al., Nat. Med. 3:1021-1023 (1997)). Cells were infected with SFV in serum-free DMEM at a multiplicity of infection of 10. One (1) hour after infection, the medium was replaced with MEMα+5% FBS (for CHO$_{695}$ cells) or DMEM+B27 supplement (for murine primary neurons). As with the previous findings relating to the overexpression of β-catenin and APP, infection with SFV encoding β-catenin had no effect on Aβ production (data not shown). These observations, particularly when combined, show that an elevated level of β-catenin is not sufficient to cause the decrease in Aβ seen with GSK-3 inhibitors.

Example 6

GSK-3 Regulates APP Processing and is Required for Aβ Production.

The foregoing data show that two structurally unrelated inhibitors of GSK-3 reduce production of secreted Aβ peptides. While the logical explanation is that these inhibitors act through inhibition of GSK-3, and therefore that GSK-3 regulates Aβ production, the possibility remains that these two agents fortuitously inhibit distinct, unknown targets involved in APP processing. Thus, to confirm that GSK-3 regulates APP processing, expression of endogenous GSK-3 was reduced using RNA interference (RNAi) (see, Elbashir et al., *Nature* 411:494-498 (2001)).

CHO-APP$_{695}$ cells were transfected with short interfering RNAs (siRNAs) directed against GSK-3α and GSK-3β as follows. RNA oligonucleotides were synthesized by Dharmacon, Inc. (Lafayette, Colo.) Sequences used were:

```
Pp-Luc sense    -5'CUU ACG CUG AGU ACU UCG AdTdT 3'    (SEQ ID NO:1);
Pp-Luc antisense -5'UCG AAG UAC UCA GCG UAA GdTdT     (SEQ ID NO:2);
GSK-3β sense    -5'AUC UUU GGA GCC ACU GAU UdTdT 3'   (SEQ ID NO:3);
GSK-3β antisense -5'AAU CAG UGG CUC CAA AGA UdTdT 3'  (SEQ ID NO:4);
GSK-3α sense    -5'UUC UAC UCC AGU GGU GAG AdTdT 3'   (SEQ ID NO:5); and
GSK-3α antisense -5'UCU CAC CAC UGG AGU AGA AdTdT 3'  (SEQ ID NO:6).
```

The dsRNA was produced using conditions described in Elbashir et al., 2001, supra. The siRNA was transfected into the CHO-APP$_{695}$ cells plated in 6-well dishes using GenePORTER transfection reagent. The siRNA (25 nM) was co-transfected with 2 μg plasmid DNA. The siRNA against pGL3-luciferase (Pp-Luc) represents control transfection. GSK-3α siRNA selectively reduces GSK-3α protein (see FIG. 3a, closed arrow). GSK-3β directed siRNA selectively reduces GSK-3β (see FIG. 3a, open arrow). Following transfection, the cells were cultured and harvested 48 hours later. GSK-3α and GSK-3β protein levels were examined using an antibody that recognized both GSK-3 isoforms (Calbiochem), and western blotted as above.

Figure 3A:
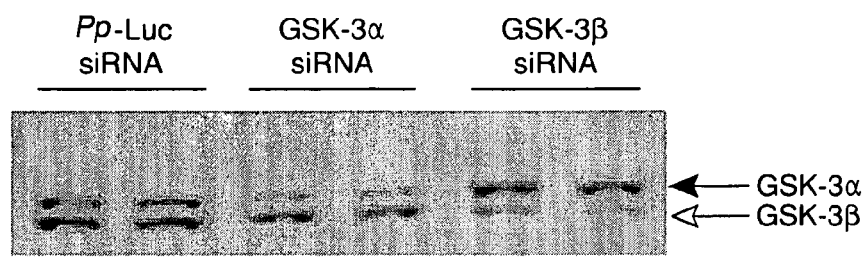
FIGS. 3a-3b show that GSK-3α is required for Aβ production.

While a control siRNA had no effect on GSK-3 expression, GSK-3-directed siRNAs reduced GSK-3 protein in an isoform-specific manner as shown in the western blot presented in FIG. 3a. Accordingly, GSK-3α is required for Aβ production.

Figure 3B:
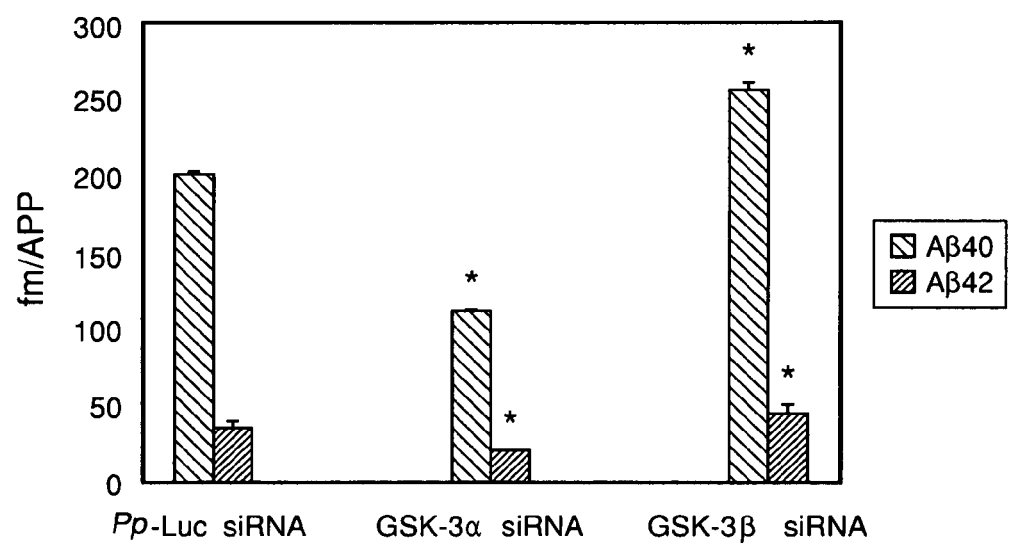

As graphically presented in FIG. 3b, Aβ levels (Aβ$_{40}$ shown in light bars; Aβ342 shown in dark bars) secreted from siRNA and transfected cells in a representative experiment, were assessed as in FIG. 1. Error bars represent standard deviation. The experiment was repeated six times with similar results. As a result, the selective reduction of GSK-3 a protein decreased Aβ$_{40}$ and Aβ$_{42}$ levels by 45% and 43%, respectively (FIG. 3b). Asterisks indicate a significant difference from control, as determined by one-way ANOVA (p<0.05).

Surprisingly, reduction of GSK-3β protein did not lead to decreased Aβ$_{40}$ and Aβ$_{42}$ levels. To the contrary, GSK-3β reduction resulted in a modest increase in levels of secreted Aβ$_{40}$ and Aβ$_{42}$. Thus, although these data further confirm that GSK-3α is required for maximal production of Aβ$_{40}$ and Aβ$_{42}$, they also suggest that GSK-3β may in certain settings antagonize APP processing.

Since either lithium treatment or GSK-3α depletion was shown to reduce Aβ$_{40}$ and Aβ$_{42}$ levels, it was important to confirm whether raising GSK-3α levels would similarly enhance Aβ$_{40}$ and Aβ$_{42}$ production as expected. To do so, CHO-APP695 cells were transfected with green fluorescent protein (GFP) or increasing amounts of GSK-3α (0.5 μg to 2.0 μg), then secreted Aβ levels were assessed as in Example 1. Overexpression of GSK-3α in CHO-APP$_{695}$ cells was found to increase Aβ$_{40}$ and Aβ$_{42}$ levels in a dose dependent manner (data not shown). Thus, levels of Aβ production were directly correlated with GSK-3α expression in both loss of function and overexpression approaches. The isoform specific depletion of GSK-3 by RNAi together with the overexpression data confirmed that GSK-3α is required for maximal APP processing.

Example 7

Effect of Lithium Treatments on Aβ Production in Cultured Neurons and in vivo in Brain Tissue of Animal Models.

In light of the foregoing examples, it was important to demonstrate that lithium blocked or reduced Aβ production in cultured neurons and in the brains of recognized animal models associated with Alzheimer's disease.

To generate NT2N neurons, a human embryonic carcinoma cell line (NTera2/D1 or NT2) was grown and maintained, essentially as described by Pleasure et al., *J. Neurosci.* 12:1802-1815 (1992). For murine primary embryonic neurons, cortices from E15 mouse brains were isolated and incubated in 0.1% trypsin/HBSS/0.5 mM EDTA, without $Ca^{2+}$ or $Mg^{2+}$ (Invitrogen, Carlsbad, Calif.). HBSS (Hank's Balanced Salt Solution; containing potassium chloride, monobasic potassium phosphate, sodium chloride, dibasic sodium phosphate, and D-glucose). Cells were mechanically dissociated using a fire-polished pipette. Cells were plated in DMEM+10% FBS (fetal bovine serum) in poly-D-lysine coated 6-well plates at a density of $10^6$ cells/well. Twenty-four (24) hours after plating, the medium was replaced with DMEM plus B27 (Invitrogen) to promote neuronal survival and inhibit growth of non-neuronal cells. Neurons were used for experiments after three (3) days in culture.

Figure 4A:
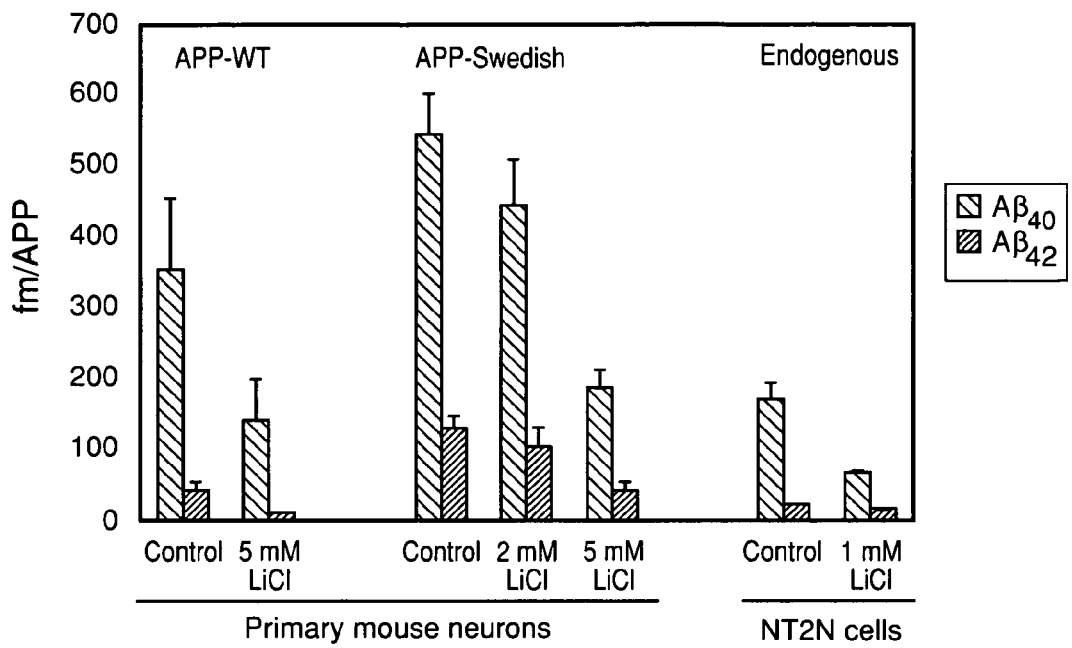
FIGS. 4a-4c graphically show that lithium blocks Aβ accumulation in cultured neurons and in the brains of mice overproducing Aβ peptides.

Primary cultures of the embryonic mouse cortical neurons were then infected with a Semliki Forest Virus (SFV) containing either wild-type APP (APP-WT) or APP with the pathogenic Swedish mutation (KM670/671NL), then treated with oral lithium (2.0 or 5.0 mM LiCl, as shown in FIG. 4a) for 24 hours. Media was collected and levels of secreted Aβ$_{40}$ (FIG. 4a; light bars) and Aβ$_{42}$ (FIG. 4a; dark bars) were measured as described above.

Production of Aβ$_{40}$ and Aβ$_{42}$ was reduced by 60% and 78%, respectively, for wild-type APP and to a similar extent for the APP-Swedish mutation (FIG. 4a). A lower, clinically relevant concentration of lithium (1.0 mM) also reduced accumulation of endogenous Aβ by as much as 60% after 3-days of culture in the neuronal NT2N cell line (FIG. 4a).

To determine the effect of oral lithium treatments on brain tissue in vivo, transgenic mice expressing pathogenic, FAD-associated forms of APP (APP-Swedish/Tg2576) were crossed to mice carrying a "knock-in" of the PS1$^{P264L}$ mutation (pS1$^{P264L}$/wt)(provided by Flood; see, Siman et al., *J. Neurosci.* 20:8717-8726 (2000)). Three-month-old heterozygous female Tg2576 /PS1$^{P264L}$/wt mice were administered LiCl (n=7) or NaCl (n=7) (300 mg/kg in 0.4 ml water, by gastric gavage once daily for 3 weeks). Animals were allowed free access to food and water, and lithium-treated mice were given free access to 450 mM NaCl solution. Animals were sacrificed three (3) hours after the final dose and tissue accumulated Aβ levels were measured after stepwise extraction of Aβ from brain cortical tissues by both RIPA-extraction (soluble fractions) and formic acid-extraction (insoluble fractions).

Briefly, the mouse cerebral cortices were lysed in RIPA buffer. Following centrifugation, insoluble material was extracted in formic acid (FA) (essentially as described by Wilson et al., *Nat. Neurosci.* 5:849-855 (2002)). RIPA- and FA-extracted samples were diluted and Aβ levels were measured by sandwich ELISA as above (Aβ sandwich ELISA obtainable from Takeda Pharmaceuticals, Osaka, Japan).

Figure 4B:
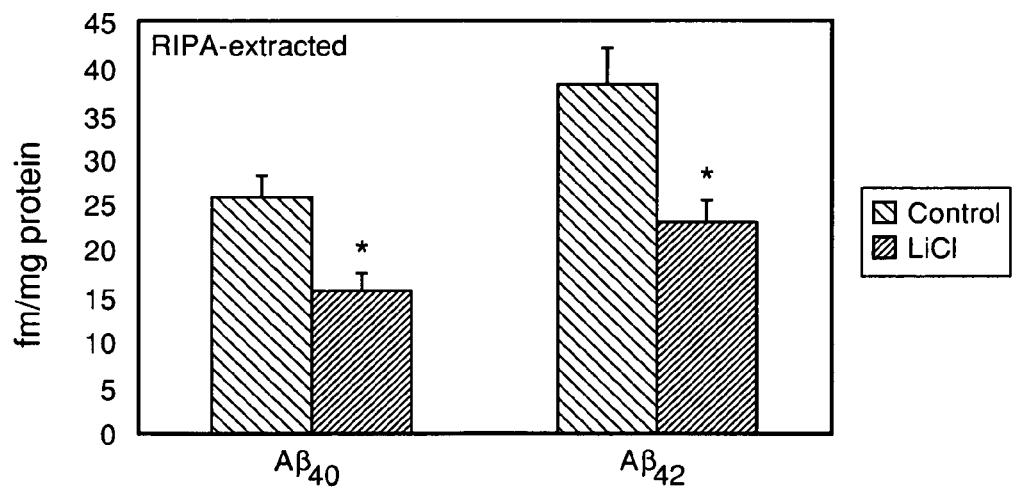
Figure 4C:
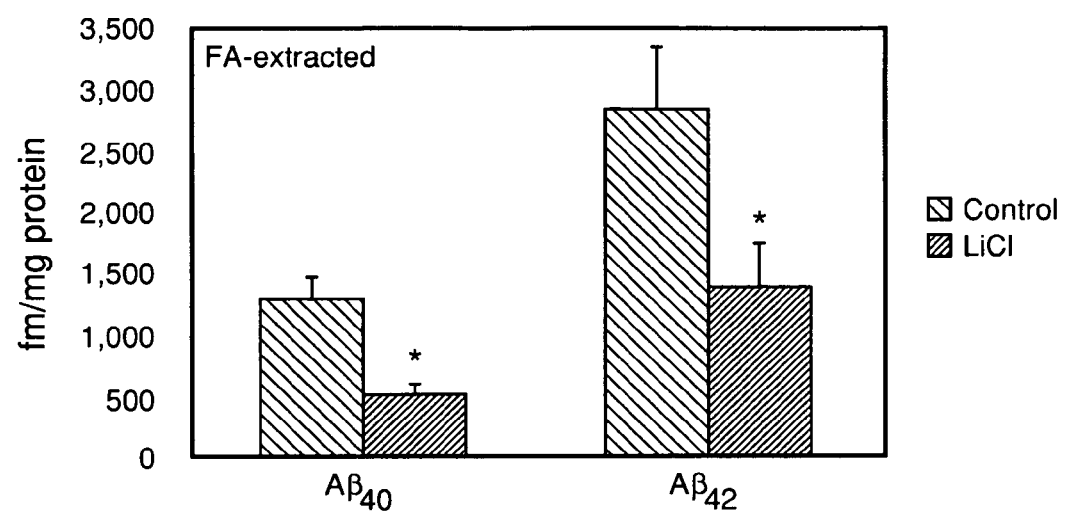

Under these conditions, serum lithium levels were 0.8-1.2 mM (FIG. 4b), which was safely within the therapeutic range for bipolar patients treated with lithium. In the lithium treated group, soluble RIPA-extracted Aβ$_{40}$ and Aβ$_{42}$ levels were each reduced by 40% (FIG. 4b). Furthermore, levels of insoluble Aβ$_{40}$ and Aβ$_{42}$ extractable with formic acid were reduced by 62% and 51%, respectively (FIG. 4c). Accordingly, this demonstrated that a clinically tolerated dose of lithium markedly reduces the tissue level of Aβ peptides (Aβ production) in both the neurons and in the brains of subjects treated with oral lithium.

The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

What is claimed is:

1. A method of inhibiting or reducing symptoms of Alzheimer's disease in a patient, comprising the steps of:
   (i) administering to the Alzheimer's disease patient a therapeutically effective composition, comprising a pharmaceutically acceptable amount of a GSK-3 inhibitor or GSK-3α-specific inhibitor, wherein the GSK-3 inhibitor or GSK-3α-specific inhibitor comprises lithium or a salt thereof;
   (ii) measuring the blocking, inhibiting or reducing production of Aβ amyloid peptides in the patient following the administering step (i); and
   (iii) determining that the administered inhibitor is sufficient to block, inhibit or reduce GSK-3 or GSK-3α activity in the patient, such that measured formation of Aβ amyloid peptides in the patient is reduced in the ranges of 30% to 60%.

2. The method of claim 1, wherein the patient is a mammal.

3. The method of claim 2, wherein the mammal is human.

4. The method of claim 1, wherein the GSK-3 inhibitor or GSK-3α-specific inhibitor comprises lithium.

5. The method of claim 1, wherein the patient's requirement for other medication to treat Alzheimer's disease and the patient's symptoms related thereto is reduced.

6. The method of claim 1, comprising the steps of:
   (i) administering to the Alzheimer's disease patient a therapeutically effective composition, comprising a pharmaceutically acceptable amount of a GSK-3 inhibitor or GSK-3α-specific inhibitor, wherein the GSK-3 inhibitor or GSK-3α-specific inhibitor comprises lithium or a salt thereof;
   (ii) measuring the blocking, inhibiting or reducing production of $A\beta_{40}$ and $A\beta_{42}$ peptide levels in the patient following the administering step (i); and
   (iii) determining that the administered inhibitor is effective for inhibiting or reducing symptoms of Alzheimer's disease in the patient, such that measured $A\beta_{40}$ and $A\beta_{42}$ peptide levels are reduced in the range of 30% to 60%.

7. The method of claim 6, wherein the GSK-3 inhibitor or GSK-3α-specific inhibitor comprises lithium.

* * * * *